(12) United States Patent
Koo

(10) Patent No.: US 7,518,728 B2
(45) Date of Patent: Apr. 14, 2009

(54) METHOD AND INSTRUMENT FOR COLLECTING FOURIER TRANSFORM (FT) RAMAN SPECTRA FOR IMAGING APPLICATIONS

(75) Inventor: Tae-Woong Koo, Cupertino, CA (US)

(73) Assignee: Intel Corporation, Santa Clara, CA (US)

( * ) Notice: Subject to any disclaimer, the term of this patent is extended or adjusted under 35 U.S.C. 154(b) by 143 days.

(21) Appl. No.: 11/239,118

(22) Filed: Sep. 30, 2005

(65) Prior Publication Data

US 2007/0076208 A1 Apr. 5, 2007

(51) Int. Cl.
G01B 9/02 (2006.01)
G01J 3/45 (2006.01)

(52) U.S. Cl. .................................................... 356/456
(58) Field of Classification Search ................. 356/451, 356/456
See application file for complete search history.

(56) References Cited

U.S. PATENT DOCUMENTS

| | | | | |
|---|---|---|---|---|
| 5,377,003 A | * | 12/1994 | Lewis et al. | 356/456 |
| 5,539,517 A | * | 7/1996 | Cabib et al. | 356/456 |
| 7,092,101 B2 | * | 8/2006 | Brady et al. | 356/456 |
| 7,092,103 B1 | * | 8/2006 | Kendrick et al. | 356/497 |
| 2002/0011566 A1 | * | 1/2002 | Nagayama et al. | 250/311 |
| 2004/0150830 A1 | * | 8/2004 | Chan | 356/479 |
| 2004/0182710 A1 | * | 9/2004 | Tanaami | 204/603 |
| 2005/0275847 A1 | * | 12/2005 | Moshe | 356/456 |
| 2006/0164649 A1 | * | 7/2006 | Rosengaus | 356/450 |
| 2007/0013916 A1 | * | 1/2007 | Kim et al. | 356/498 |
| 2007/0224526 A1 | * | 9/2007 | Brunner et al. | 430/30 |

* cited by examiner

Primary Examiner—Patrick J Connolly
(74) Attorney, Agent, or Firm—Pillsbury Winthrop Shaw Pittman LLP

(57) ABSTRACT

An instrument having an illumination source configured to illuminate a field of illumination on a surface of a substrate that is configured to hold a sample. The field of illumination typically has a diameter greater than 1 micron or an area greater than that of at least one pad of an array. The instrument also includes an interferometer, and a detectors. The instrument is configured to perform Fourier transform imaging without single spot scanning or without line scanning. Additionally, the instrument may include an illumination light source, an array detector and spectral processing electronics. A method of collecting Fourier transform (FT) data is also disclosed.

62 Claims, 17 Drawing Sheets

Prior Art

Prior Art

Prior Art

US 7,518,728 B2

METHOD AND INSTRUMENT FOR COLLECTING FOURIER TRANSFORM (FT) RAMAN SPECTRA FOR IMAGING APPLICATIONS

RELATED APPLICATIONS

This application is related to U.S. application Ser. No. 11/239,100, entitled "Miniaturized spectrometer using optical waveguide and integrated Raman system on-chip," filed herewith, which is incorporated herein by reference.

FIELD OF INVENTION

The embodiments of the invention relate to an integrated device for Raman spectroscopy and to a method to simultaneously perform FT-Raman measurements of a large area of a sample. When a sufficient number of measurement spots over a certain area of the sample are measured, the embodiments of the invention allow Raman-imaging of the sample. The invention transcends several scientific disciplines such as polymer chemistry, biochemistry, molecular biology, medicine and medical diagnostics.

BACKGROUND

An optical spectrometer is a device that can analyze the incoming light by frequency (wavelength) components and their intensities. In general, there are two types of spectrometers: dispersive and interferometric. A dispersive spectrometer has an optically dispersive component (e.g. prism or grating) to spatially disperse the incoming light as a function of wavelength. The dispersed light is collected by multichannel detectors. An interferometric spectrometer records the interferogram generated by the incoming light, and mathematically converts the interferogram to a spectrum. An example of an interferometric spectrometer is a Fourier-transform infrared spectrometer (FTIR) based on a Michelson interferometer.

Conventional optical spectrometers when used for imaging adopt a spot scanning process, wherein a single spot of light is illuminated on the surface of the surface of the sample for collecting multiwavelength optical data and/or image data, such as Raman or fluorescence data. The single spot of laser light on a surface of the sample of a conventional spot scanning spectrometer has a diameter of about 200 nanometers to 1 micron, when the spectrometer is used for imaging. When the sample is large, such as a biomolecular sample, spot scanning can only be performed at significantly limited speeds. This is because state-of-the-art spot scanning methods involve sample positioning after a spectrum is collected from each spot, which delays the scanning when many (e.g. >1000) spots need to be scanned for imaging application.

FIG. 1 shows the flow diagram of the conventional spot scanning system. A sample is positioned for measurement of an optical property at 102. A spectrum including a range of wavelengths or wavenumbers is collected at 104 typically by scanning through the range in more or less narrow increments. When the last position has not yet been reached at 106, then the process continues at 108 by collecting a spectrum for a next spot by repeating 104 for as many spots as may exist on the surface of an array.

FIG. 2 illustrates schematically a conventional single spot scanning system. An array 202 includes multiple pads 204. An array 202 may include more than 100 spots, particularly when a detailed image of the sample is desired. A sample beam 206 is illustrated with a dotted line in FIG. 2 transmitting a dichroic filter 208 and focusing lens 210 onto the spot 204. A Raman signal, fluorescence signal or other optical signal 212 emitted from the sample as a result of the illumination by the beam 206 is collected by first transmitting the lens 210 and reflecting from the dichroic filter 208. The signal 212 is then focused by a lens 214 to a spectrograph (e.g. Czerny-Terner spectrograph) and detector system 216. The sample is moved in two directions during the course of a complete scan as illustrated by the two bi-directional arrows 218. Alternatively, the laser spot on the sample can be moved instead of the sample by a scanning mirror (not shown) similar to the method used in confocal scanning.

Line scanning may be used, as illustrated at FIG. 3, in a faster process than the spot scanning technique of illustrated at FIGS. 1 and 2. A linear illumination 304 of the sample 202 is provided by a beam 306 that is passed through a cylindrical lens 307, filter 308 and lens 310. A linear emission 312 from the sample surface 302 is then collected by passing through focusing lens 310, reflecting from filter 308, transmitting lens 314 and being incident at linear imaging spectrograph (e.g. Czerny-Terner) and two-dimensional array detector 316. The sample is only moved in one direction, as illustrated by the single bidirectional arrow 318, in order to achieve an image.

A single channel Fourier-transform (FT) Raman spectrometry may be performed using a Thermo Nicolet™ system. This instrument includes a single channel detector and performs spot scanning in accordance with FIG. 1.

SUMMARY OF THE INVENTION

The present invention provides an instrument comprising (a) an illumination source configured to illuminate a field of illumination on a surface of a substrate that is configured to hold a sample, the field of illumination having a diameter greater than 1 microns, (b) an interferometer, and (c) a detector, wherein the detector is an array detector comprising a plurality of detectors or a single detector having multiple channels, and further wherein the instrument is configured to perform Fourier transform imaging without single spot scanning or without line scanning.

The present invention also provides an instrument comprising (a) an illumination source configured to illuminate a field of illumination on a surface of a substrate that is configured to hold a sample, the field of illumination having an area greater than that of at least one pad of an array, (b) an interferometer and (c) a detector, wherein the detector is an array detector comprising a plurality of detectors or a single detector having multiple channels, and further wherein the instrument is configured to perform Fourier transform imaging without single spot scanning or without line scanning.

The present invention also provides a method of collecting Fourier transform (FT) data, comprising (a) illuminating a field of illumination in a plane containing a sample that emits an electromagnetic radiation, the field of illumination having a diameter greater than 1 microns, (b) transforming the electromagnetic radiation emitted from the sample, (c) detecting an interferogram, and (d) transforming the interfering patterns into the original spectrum by calculating Fourier transformation of the interfering patterns wherein the method performs the FT data collection without single spot scanning or without line scanning.

The present invention also provides a method of collecting Fourier transform (FT) data, comprising (a) illuminating a field of illumination in a plane containing a sample that emits an electromagnetic radiation, the field of illumination having an area greater than that of at least one pad of an array, (b) transforming the electromagnetic radiation emitted from the sample into an interferogram, (c) detecting the interferogram, and (d) transforming the interferogram into the emission spectrum wherein the method performs the FT data collection without single spot scanning or without line scanning.

The present invention also provides a method of collecting Fourier Transform (FT) data with an optical imaging system, comprising (a) simultaneously exposing to an illumination source multiple pads that emit light at one or more wavelengths different from the illumination wavelength (b) directing the emitted light from the multiple pads along a predetermined optical path (c) interferometrically sampling the emitted light and scanning a spectral range that includes the one or more wavelengths of the light emitted from the multiple pads (d) detecting the emitted light from the multiple pads simultaneously and (e) collecting FT data corresponding to the detected light.

DETAILED DESCRIPTION

As used in the specification and claims, the singular forms "a", "an" and "the" include plural references unless the context clearly dictates otherwise. For example, the term "an array" may include a plurality of arrays unless the context clearly dictates otherwise.

Figure 1:
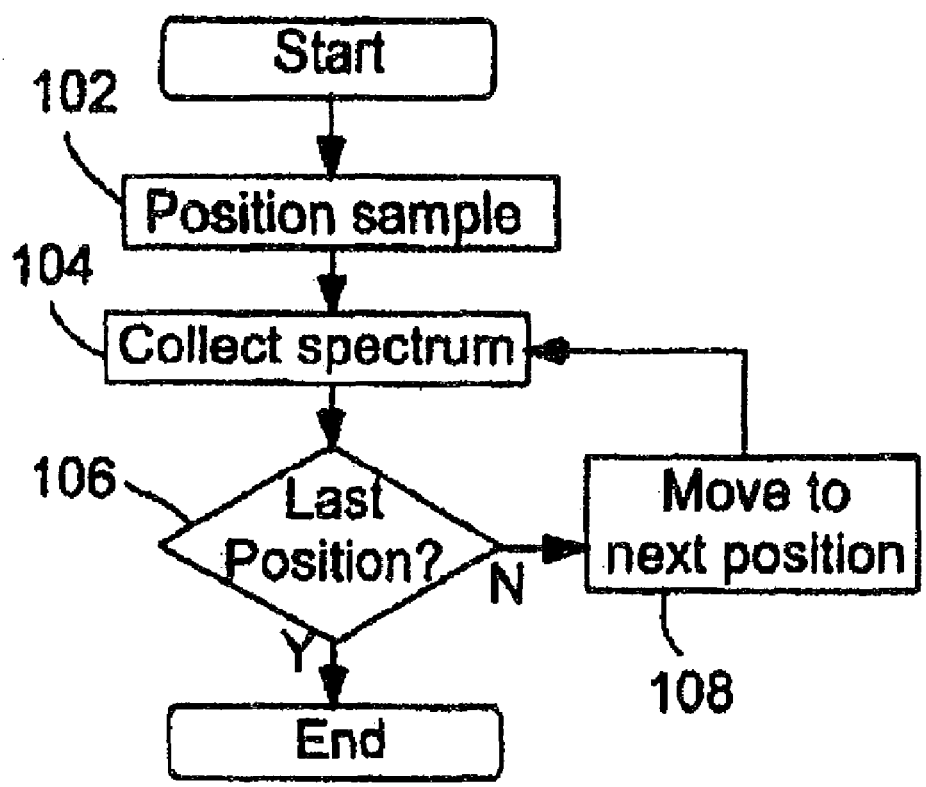
FIG. 1 is a flow diagram that illustrates a conventional spot scanning method.
Figure 2:
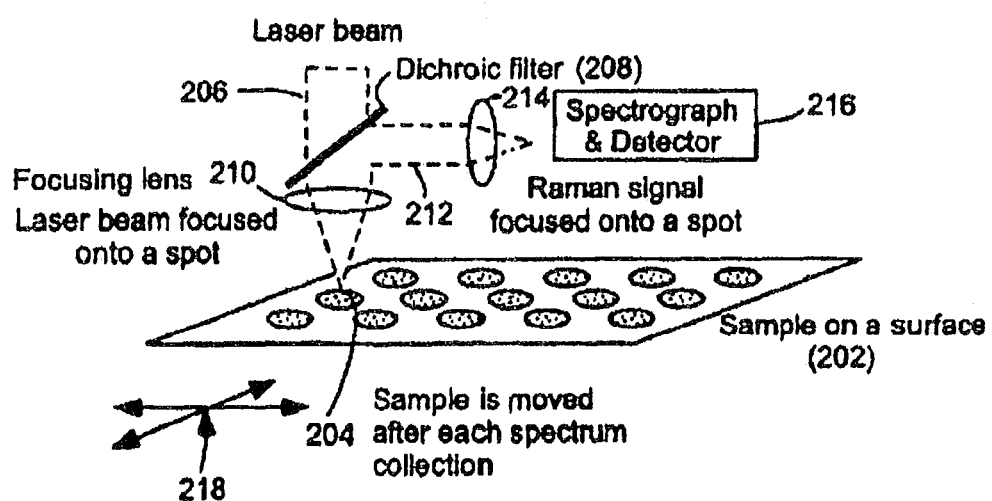
FIG. 2 schematically illustrates a conventional spot scanning system.

"Single spot scanning" refers to the apparatus and method the conventional spot scanning system described in the Background with reference to FIG. 2.

Figure 3:
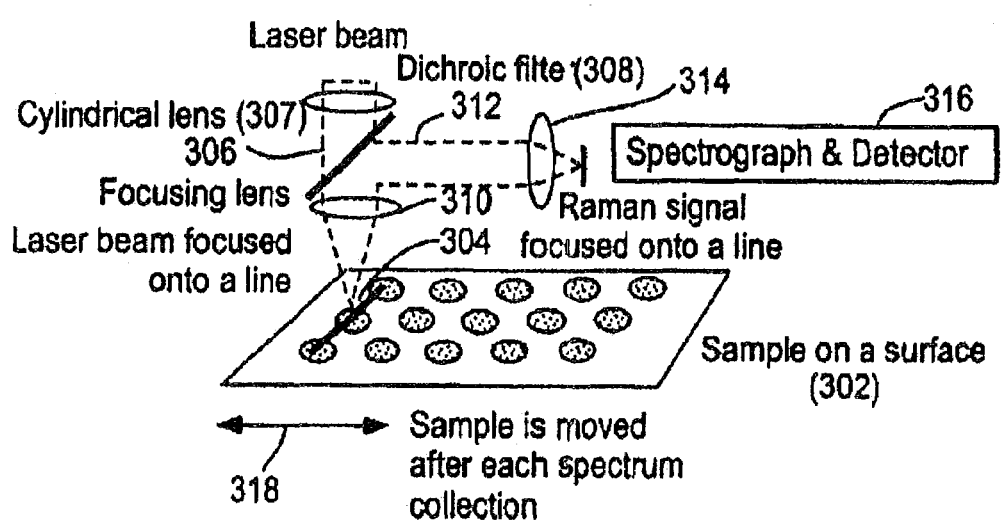
FIG. 3 schematically illustrates a conventional line scanning system.

"Line scanning" refers to the apparatus and method the conventional line scanning system described in the Background with reference to FIG. 3.

An "array," "macroarray" or "microarray" is an intentionally created collection of molecules which can be prepared either synthetically or biosynthetically. The molecules in the array can be identical or different from each other. The array can assume a variety of formats, e.g., libraries of soluble molecules; libraries of compounds tethered to resin beads, silica chips, or other solid supports. The array could either be a macroarray or a microarray, depending on the size of the pads on the array. A macroarray generally contains pad sizes of about 300 microns or larger and can be easily imaged by gel and blot scanners. A microarray would generally contain pad sizes of less than 300 microns.

"Solid support," "support," and "substrate" refer to a material or group of materials having a rigid or semi-rigid surface or surfaces. In some aspects, at least one surface of the solid support will be substantially flat, although in some aspects it may be desirable to physically separate synthesis regions for different molecules with, for example, wells, raised regions, pins, etched trenches, or the like. In certain aspects, the solid support(s) will take the form of beads, resins, gels, microspheres, or other geometric configurations.

The term "target" or "target molecule" refers to a molecule of interest that is to be analyzed, e.g., a nucleotide, an oligonucleotide, a polynucleotide, a peptide, or a protein. The target or target molecule could be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to molecular probes such as chemically modified carbon nanotubes, carbon nanotube bundles, nanowires, nanoclusters or nanoparticles. The target molecule may be fluorescently labeled DNA or RNA.

The term "probe" or "probe molecule" refers to a molecule that binds to a target molecule for the analysis of the target. The probe or probe molecule is generally, but not necessarily, has a known molecular structure or sequence. The probe or probe molecule is generally, but not necessarily, attached to the substrate of the array. The probe or probe molecule is typically a nucleotide, an oligonucleotide, a polynucleotide, a peptide, or a protein, including, for example, cDNA or pre-synthesized polynucleotide deposited on the array. Probes molecules are biomolecules capable of undergoing binding or molecular recognition events with target molecules. (In some references, the terms "target" and "probe" are defined opposite to the definitions provided here.) The polynucleotide probes require only the sequence information of genes, and thereby can exploit the genome sequences of an organism. In cDNA arrays, there could be cross-hybridization due to sequence homologies among members of a gene family. Polynucleotide arrays can be specifically designed to differentiate between highly homologous members of a gene family as well as spliced forms of the same gene (exon-specific). Polynucleotide arrays of the embodiment of this invention could also be designed to allow detection of mutations and single nucleotide polymorphism. A probe or probe molecule can be a capture molecule.

The term "capture molecule" refers to a molecule that is immobilized on a surface. The capture molecule is generally, but not necessarily, binds to a target or target molecule. The capture molecule is typically a nucleotide, an oligonucleotide, a polynucleotide, a peptide, or a protein, but could also be a small molecule, biomolecule, or nanomaterial such as but not necessarily limited to a small molecule that is biologically active, nucleic acids and their sequences, peptides and polypeptides, as well as nanostructure materials chemically modified with biomolecules or small molecules capable of binding to a target molecule that is bound to a probe molecule to form a complex of the capture molecule, target molecule and the probe molecule. The capture molecule may be fluorescently labeled DNA or RNA. The capture molecule may or may not be capable of binding to just the target molecule or just the probe molecule.

The terms "die," "polymer array chip," "DNA array," "array chip," "DNA array chip," or "bio-chip" are used interchangeably and refer to a collection of a large number of probes arranged on a shared substrate which could be a portion of a silicon wafer, a nylon strip or a glass slide.

The term "chip" or "microchip" refers to a microelectronic device made of semiconductor material and having one or more integrated circuits or one or more devices. A "chip" or "microchip" is typically a section of a wafer and made by slicing the wafer. A "chip" or "microchip" may comprise many miniature transistors and other electronic components on a single thin rectangle of silicon, sapphire, germanium, silicon nitride, silicon germanium, or of any other semiconductor material. A microchip can contain dozens, hundreds, or millions of electronic components.

The term "molecule" generally refers to a macromolecule or polymer as described herein. However, arrays comprising single molecules, as opposed to macromolecules or polymers, are also within the scope of the embodiments of the invention.

"Predefined region" or "spot" or "pad" refers to a localized area on a solid support. The pad could be intended to be used for formation of a selected molecule and is otherwise referred to herein in the alternative as a "selected" region. The pad may have any convenient shape, e.g., circular, rectangular, elliptical, wedge-shaped, etc. For the sake of brevity herein, "predefined regions" are sometimes referred to simply as "regions," "spots," or "pads." In some embodiments, a predefined region and, therefore, the area upon which each distinct molecule is synthesized is smaller than about 1 $cm^2$ or less than 1 $mm^2$, and still more preferably less than 0.5 $mm^2$. In most preferred embodiments the regions have an area less than about 10,000 $\mu m^2$ or, more preferably, less than 100 $\mu m^2$, and even more preferably less than 10 $\mu m^2$ or less than 1 $\mu m^2$. Additionally, multiple copies of the polymer will typically be synthesized within any preselected region. The number of copies can be in the hundreds to the millions. A pad could contain an electrode to generate an electrochemical reagent, a working electrode to synthesize a polymer and a confinement electrode to confine the generated electrochemical reagent. The electrode to generate the electrochemical reagent could be of any shape, including, for example, circular, flat disk shaped and hemisphere shaped.

"Micro-Electro-Mechanical Systems (MEMS)" is the integration of mechanical elements, sensors, actuators, and electronics on a common silicon substrate through microfabrication technology. While the electronics are fabricated using integrated circuit (IC) process sequences (e.g., CMOS, Bipolar, or BICMOS processes), the micromechanical components could be fabricated using compatible "micromachining" processes that selectively etch away parts of the silicon wafer or add new structural layers to form the mechanical and electromechanical devices. Microelectronic integrated circuits can be thought of as the "brains" of a system and MEMS augments this decision-making capability with "eyes" and "arms", to allow microsystems to sense and control the environment. Sensors gather information from the environment through measuring mechanical, thermal, biological, chemical, optical, and magnetic phenomena. The electronics then process the information derived from the sensors and through some decision making capability direct the actuators to respond by moving, positioning, regulating, pumping, and filtering, thereby controlling the environment for some desired outcome or purpose. Because MEMS devices are manufactured using batch fabrication techniques similar to those used for integrated circuits, unprecedented levels of functionality, reliability, and sophistication can be placed on a small silicon chip at a relatively low cost.

"Microprocessor" is a processor on an integrated circuit (IC) chip. The processor may be one or more processor on one or more IC chip. The chip is typically a silicon chip with thousands of electronic components that serves as a central processing unit (CPU) of a computer or a computing device.

A "macromolecule" or "polymer" comprises two or more monomers covalently joined. The monomers may be joined one at a time or in strings of multiple monomers, ordinarily known as "oligomers." Thus, for example, one monomer and a string of five monomers may be joined to form a macromolecule or polymer of six monomers. Similarly, a string of fifty monomers may be joined with a string of hundred monomers to form a macromolecule or polymer of one hundred and fifty monomers. The term polymer as used herein includes, for example, both linear and cyclic polymers of nucleic acids, polynucleotides, polynucleotides, polysaccharides, oligosaccharides, proteins, polypeptides, peptides, phospholipids and peptide nucleic acids (PNAs). The peptides include those peptides having either $\alpha$-, $\beta$-, or $\omega$-amino acids. In addition, polymers include heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure.

A "nanomaterial" as used herein refers to a structure, a device or a system having a dimension at the atomic, molecular or macromolecular levels, in the length scale of approximately 1-100 nanometer range. Preferably, a nanomaterial has properties and functions because of the size and can be manipulated and controlled on the atomic level.

A "carbon nanotube" refers to a fullerene molecule having a cylindrical or toroidal shape. A "fullerene" refers to a form of carbon having a large molecule consisting of an empty cage of sixty or more carbon atoms.

The term "biomolecule" refers to any organic molecule that is part of a living organism. Biomolecules includes a nucleotide, a polynucleotide, an oligonucleotide, a peptide, a protein, a ligand, a receptor, among others. A "complex of a biomolecule" refers to a structure made up of two or more types of biomolecules. Examples of a complex of biomolecule include a cell or viral particles. A cell can include bacteria, fungi, animal mammalian cell, for example.

The term "nucleotide" includes deoxynucleotides and analogs thereof. These analogs are those molecules having some structural features in common with a naturally occurring nucleotide such that when incorporated into a polynucleotide sequence, they allow hybridization with a complementary polynucleotide in solution. Typically, these analogs are derived from naturally occurring nucleotides by replacing and/or modifying the base, the ribose or the phosphodiester moiety. The changes can be tailor-made to stabilize or destabilize hybrid formation, or to enhance the specificity of hybridization with a complementary polynucleotide sequence as desired, or to enhance stability of the polynucleotide.

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribopolynucleotide (DNA), ribopolynucleotide (RNA), or DNA copies of ribopolynucleotide (CDNA) which may be isolated from natural sources, recombinantly produced, or artificially synthesized. A further example of a polynucleotide of the embodiments of the invention may be polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as "nucleotide polymers."

An "oligonucleotide" is a polynucleotide having 2 to 20 nucleotides. Analogs also include protected and/or modified monomers as are conventionally used in polynucleotide synthesis. As one of skill in the art is well aware, polynucleotide synthesis uses a variety of base-protected nucleoside derivatives in which one or more of the nitrogens of the purine and pyrimidine moiety are protected by groups such as dimethoxytrityl, benzyl, tert-butyl, isobutyl and the like.

For instance, structural groups are optionally added to the ribose or base of a nucleoside for incorporation into a polynucleotide, such as a methyl, propyl or allyl group at the 2'-O position on the ribose, or a fluoro group which substitutes for the 2'-O group, or a bromo group on the ribonucleoside base. 2'-O-thyloligoribonucleotides (2'-O-MeORNs) have a higher affinity for complementary polynucleotides (especially RNA) than their unmodified counterparts. Alternatively, deazapurines and deazapyrimidines in which one or more N atoms of the purine or pyrimidine heterocyclic ring are replaced by C atoms can also be used.

The phosphodiester linkage or "sugar-phosphate backbone" of the polynucleotide can also be substituted or modified, for instance with methyl phosphonates, O-methyl phosphates or phosphororthioates. Another example of a polynucleotide comprising such modified linkages for purposes of this disclosure includes "peptide polynucleotides" in which a polyamide backbone is attached to polynucleotide bases, or modified polynucleotide bases. Peptide polynucleotides which comprise a polyamide backbone and the bases found in naturally occurring nucleotides are commercially available.

Nucleotides with modified bases can also be used in the embodiments of the invention. Some examples of base modifications include 2-aminoadenine, 5-methylcytosine, 5-(propyn-1-yl)cytosine, 5-(propyn-1-yl)uracil, 5-bromouracil, 5-bromocytosine, hydroxymethylcytosine, methyluracil, hydroxymethyluracil, and dihydroxypentyluracil which can be incorporated into polynucleotides in order to modify binding affinity for complementary polynucleotides.

Groups can also be linked to various positions on the nucleoside sugar ring or on the purine or pyrimidine rings which may stabilize the duplex by electrostatic interactions with the negatively charged phosphate backbone, or through interactions in the major and minor groves. For example, adenosine and guanosine nucleotides can be substituted at the $N^2$ position with an imidazolyl propyl group, increasing duplex stability. Universal base analogues such as 3-nitropyrrole and 5-nitroindole can also be included. A variety of modified polynucleotides suitable for use in the embodiments of the invention are described in the literature.

When the macromolecule of interest is a peptide, the amino acids can be any amino acids, including $\alpha$, $\beta$, or $\omega$-amino acids. When the amino acids are $\alpha$-amino acids, either the L-optical isomer or the D-optical isomer may be used. Additionally, unnatural amino acids, for example, $\beta$-alanine, phenylglycine and homoarginine are also contemplated by the embodiments of the invention. These amino acids are well-known in the art.

A "peptide" is a polymer in which the monomers are amino acids and which are joined together through amide bonds and alternatively referred to as a polypeptide. In the context of this specification it should be appreciated that the amino acids may be the L-optical isomer or the D-optical isomer. Peptides are two or more amino acid monomers long, and often more than 20 amino acid monomers long.

A "protein" is a long polymer of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies.

The term "sequence" refers to the particular ordering of monomers within a macromolecule and it may be referred to herein as the sequence of the macromolecule.

The term "hybridization" refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." For example, hybridization refers to the formation of hybrids between a probe polynucleotide (e.g., a polynucleotide of the invention which may include substitutions, deletion, and/or additions) and a specific target polynucleotide (e.g., an analyte polynucleotide) wherein the probe preferentially hybridizes to the specific target polynucleotide and substantially does not hybridize to polynucleotides consisting of sequences which are not substantially complementary to the target polynucleotide. However, it will be recognized by those of skill that the minimum length of a polynucleotide desired for specific hybridization to a target polynucleotide will depend on several factors: G/C content, positioning of mismatched bases (if any), degree of uniqueness of the sequence as compared to the population of target polynucleotides, and chemical nature of the polynucleotide (e.g., methylphosphonate backbone, phosphorothiolate, etc.), among others.

Methods for conducting polynucleotide hybridization assays have been well developed in the art. Hybridization assay procedures and conditions will vary depending on the application and are selected in accordance with the general binding methods known in the art.

It is appreciated that the ability of two single stranded polynucleotides to hybridize will depend upon factors such as their degree of complementarity as well as the stringency of the hybridization reaction conditions.

As used herein, "stringency" refers to the conditions of a hybridization reaction that influence the degree to which polynucleotides hybridize. Stringent conditions can be selected that allow polynucleotide duplexes to be distinguished based on their degree of mismatch. High stringency is correlated with a lower probability for the formation of a duplex containing mismatched bases. Thus, the higher the stringency, the greater the probability that two single-stranded polynucleotides, capable of forming a mismatched duplex, will remain single-stranded. Conversely, at lower stringency, the probability of formation of a mismatched duplex is increased.

The appropriate stringency that will allow selection of a perfectly-matched duplex, compared to a duplex containing one or more mismatches (or that will allow selection of a particular mismatched duplex compared to a duplex with a higher degree of mismatch) is generally determined empirically. Means for adjusting the stringency of a hybridization reaction are well-known to those of skill in the art.

A "ligand" is a molecule that is recognized by a particular receptor. Examples of ligands that can be investigated by this invention include, but are not restricted to, agonists and antagonists for cell membrane receptors, toxins and venoms, viral epitopes, hormones, hormone receptors, peptides, enzymes, enzyme substrates, cofactors, drugs (e.g. opiates, steroids, etc.), lectins, sugars, polynucleotides, nucleic acids, oligosaccharides, proteins, and monoclonal antibodies.

A "receptor" is molecule that has an affinity for a given ligand. Receptors may-be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term "receptors" is used herein, no difference in meaning is intended. A "Ligand Receptor Pair" is formed when two macromolecules have combined through molecular recognition to form a complex. Other examples of receptors which can be investigated by this invention include but are not restricted to:

a) Microorganism receptors: Determination of ligands which bind to receptors, such as specific transport proteins or enzymes essential to survival of microorganisms, is useful in developing a new class of antibiotics. Of particular value would be antibiotics against opportunistic fungi, protozoa, and those bacteria resistant to the antibiotics in current use.

b) Enzymes: For instance, one type of receptor is the binding site of enzymes such as the enzymes responsible for cleaving neurotransmitters; determination of ligands which bind to certain receptors to modulate the action of the enzymes which cleave the different neurotransmitters is useful in the development of drugs which can be used in the treatment of disorders of neurotransmission.

c) Antibodies: For instance, the invention may be useful in investigating the ligand-binding site on the antibody molecule which combines with the epitope of an antigen of interest; determining a sequence that mimics an antigenic epitope may lead to the-development of vaccines of which the immunogen is based on one or more of such sequences or lead to the development of related diagnostic agents or compounds useful in therapeutic treatments such as for auto-immune diseases (e.g., by blocking the binding of the "anti-self" antibodies).

d) Nucleic Acids: Sequences of nucleic acids may be synthesized to establish DNA or RNA binding sequences.

e) Catalytic Polypeptides: Polymers, preferably polypeptides, which are capable of promoting a chemical reaction involving the conversion of one or more reactants to one or more products. Such polypeptides generally include a binding site specific for at least one reactant or reaction intermediate and an active functionality proximate to the binding site, which functionality is capable of chemically modifying the bound reactant.

f) Hormone receptors: Examples of hormones receptors include, e.g., the receptors for insulin and growth hormone. Determination of the ligands which bind with high affinity to a receptor is useful in the development of, for example, an oral replacement of the daily injections which diabetics take to relieve the symptoms of diabetes. Other examples are the vasoconstrictive hormone receptors; determination of those ligands which bind to a receptor may lead to the development of drugs to control blood pressure.

g) Opiate receptors: Determination of ligands which bind to the opiate receptors in the brain is useful in the development of less-addictive replacements for morphine and related drugs.

As used herein, "Raman-active organic compound" refers to an organic molecule that produces a unique surface-enhanced Raman scattering signature in response to excitation by a laser. In certain embodiments, Raman-active organic compounds are polycyclic aromatic or heteroaromatic compounds. Typically the Raman-active organic compound has a molecular weight less than about 300 Daltons.

Additional, non-limiting examples of Raman-active organic compounds include TRIT (tetramethyl rhodamine isothiol), NBD (7-nitrobenz-2-oxa-1, 3-diazole), Texas Red dye, phthalic acid, terephthalic acid, isophthalic acid, cresyl fast violet, cresyl blue violet, brilliant cresyl blue, para-aminobenzoic acid, erythrosine, biotin, digoxigenin, 5-carboxy-4',5'-dichloro-2',7'-dimethoxy fluorescein, 5-carboxy-2',4',5',7'-tetrachlorofluorescein, 5-carboxyfluorescein, 5-carboxy rhodamine, 6-carboxyrhodamine, 6-carboxytetramethyl amino phthalocyanines, azomethines, cyanines, xanthines, succinylfluoresceins, aminoacridine, and the like.

In certain embodiments, the Raman-active compound is adenine, adenine, 4-amino-pyrazolo(3,4-d)pyrimidine, 2-fluoroadenine, N6-benzolyadenine, kinetin, dimethyl-allyl-amino-adenine, zeatin, bromo-adenine, 8-aza-adenine, 8-azaguanine, 6-mercaptopurine, 4-amino-6-mercaptopyrazolo(3,4-d)pyrimidine, 8-mercaptoadenine, or 9-amino-acridine 4-amino-pyrazolo(3,4-d)pyrimidine, or 2-fluoroadenine. In one embodiment, the Raman-active compound is adenine.

The "fluorescent compounds" can include, but are not limited to, dyes, intrinsically fluorescent proteins, lanthanide phosphors, and the like. Dyes, for example, include rhodamine and derivatives, such as Texas Red, ROX (6-carboxy-X-rhodamine), rhodamine-NHS, and TAMRA (5/6-carboxytetramethyl rhodamine NHS); fluorescein and derivatives, such as 5-bromomethyl fluorescein and FAM (5'-carboxyfluorescein NHS), Lucifer Yellow, IAEDANS, 7-Me$_2$, N-coumarin-4-acetate, 7-OH-4-CH$_3$-coumarin-3-acetate, 7-NH$_2$-4CH$_3$-coumarin-3-acetate (AMCA), monobromobimane, pyrene trisulfonates, such as Cascade Blue, and monobromotrimethyl-ammoniobimane.

The term "complementary" refers to the topological compatibility or matching together of interacting surfaces of a ligand molecule and its receptor. Thus, the receptor and its ligand can be described as complementary, and furthermore, the contact surface characteristics are complementary to each other.

The term "waveguide" refers to a device that controls the propagation of an electromagnetic wave so that the wave is forced to follow a path defined by the physical structure of the guide. Generally speaking, the electric and magnetic fields of an electromagnetic wave have a number of possible arrangements when the wave is traveling through a waveguide. Each of these arrangements is known as a mode of propagation. Optical waveguides are used at optical frequencies. An "optical waveguide" is any structure having the ability to guide optical energy. Optical waveguides may be (a) thin-film deposits used in integrated optical circuits (IOCs) or (b) optical fibers.

The term "optical switch" refers to a switch that enables signals in optical fibers or integrated optical circuits (IOCs) to be selectively switched from one circuit to another. An optical switch may operate by (a) mechanical means, such as physically shifting an optical fiber to drive one or more alternative fibers, or (b) electro-optic effects, magneto-optic effects, or other methods. Slow optical switches, such as those using moving fibers, may be used for alternate routing of an optical transmission path. Fast optical switches, such as those using electro-optic or magneto-optic effects, may be used to perform logic operations. One type of an optical switch is a thin film optical switch, which is a switch having multilayered films of material of different optical characteristics, that is capable of switching transmitted light by using electro-optic, electro-acoustic, or magneto-optic effects to obtain signal switching, and is usually used as a component in integrated optical circuits. Thin-film optical switches may support only one propagation mode.

The term "PIN diode" refers to positive-intrinsic-negative diode—typically, a photodiode with a large, neutrally doped intrinsic region sandwiched between p-doped and n-doped semiconducting regions. A PIN diode exhibits an increase in its electrical conductivity as a function of the intensity, wavelength, and modulation rate of the incident radiation. A PIN diode is also called photodiode.

The terms "spectrum" or "spectra" refer to the intensities of electromagnetic radiation as a function of wavelength or other equivalent units, such as wavenumber, frequency, and energy level.

The term "spectrometer" refers to an instrument equipped with scales for measuring wavelengths or intensities of electromagnetic radiations at a certain wavelength or wavelengths.

The term "dispersive spectrometer" refers to a spectrometer that analyzes electromagnetic radiations generates spectra by optically dispersing the incoming radiation into its frequency or spectral components. Dispersive spectrometers can be further classified into two types: monochromators and spectrographs. A monochromator uses a single detector, narrow slit(s) (usually two, one at the entrance and another at the exit port), and a rotating dispersive element allowing the user to observe a selected range of wavelength. A spectrograph, on the other hand, uses an array of detector elements and a stationary dispersive element. In this case, the slit shown in the figure is removed, and spectral elements over a wide range of wavelengths are obtained at the same time, therefore providing faster measurements with a more expensive detection system.

The term "dispersive element" refers to a component of a dispersive spectrometer that can disperse electromagnetic radiation such a light. Dispersive elements include prisms and gratings.

The term "interferometer" refers to an instrument that uses the principle of interference of electromagnetic waves for purposes of measurement. For example, it could be any of several optical, acoustic, or radio frequency instruments that use interference phenomena between a reference wave and an experimental wave or between two parts of an experimental wave to determine wavelengths and wave velocities, measure very small distances and thicknesses, and calculate indices of refraction.

The term "interferometric spectrometer" refers to a spectrometer that records the interferogram generated by the incoming light, and mathematically converts the interferogram to a spectrum.

The term "non-dispersive element" refers to an interferometer that does not disperse electromagnetic radiation in spatial domain but instead creates an interferogram by creating a phase shift in the electromagnetic radiation.

The term "Fourier transform spectrometer" refers to a spectrometer used for Fourier transform spectroscopy, which is a measurement technique whereby spectra are collected based on the response from a pulse of electromagnetic radiation. It can be applied to variety of types of spectroscopy including infrared spectroscopy (FTIR), nuclear magnetic resonance, and electron spin resonance spectroscopy. Fourier transform spectroscopy can be more sensitive and has a much shorter sampling time than conventional spectroscopic techniques. For example, in a conventional (or "continuous wave") nucleic magnetic resonance spectrometer, a sample is exposed to electromagnetic radiation and the response (usually the intensity of transmitted radiation) is monitored. The energy of the radiation is varied over the desired range and the response is plotted as a function of radiation energy (or frequency). At certain resonant frequencies characteristic of the specific sample, the radiation will be absorbed resulting in a series of peaks in the spectrum, which can then be used to identify the sample. (In magnetic spectroscopy, the magnetic field is often varied instead of the frequency of the incident radiation, though the spectra are effectively the same as if the field had been kept constant and the frequency varied. This is largely a question of experimental convenience.) Instead of varying the energy of the electromagnetic radiation, Fourier Transform nucleic magnetic resonance spectroscopy exposes the sample to a single pulse of radiation and measures the response. The resulting signal, called a free induction decay, contains a rapidly decaying composite of all possible frequencies. Due to resonance by the sample, resonant frequencies will be dominant in the signal and by performing a mathematical operation called a Fourier transform on the signal the frequency response can be calculated. In this way the Fourier transform nucleic magnetic resonance spectrometer can produce the same kind of spectrum as a conventional spectrometer, but generally in a much shorter time.

The term "optical bench" refers to an apparatus for observation and measurement of optical phenomena. For example, it could be an apparatus such as a special table or rigid beam, for the precise positioning of light sources, screens, and optical instruments used for optical and photometric studies, having a ruled bar to which these devices can be attached and along which they can be readily adjusted.

The term "full width at half-maximum" (FWHM) is a parameter commonly used to describe the width of a "bump" or a "peak" on a curve or function. It is given by the distance between points on the curve at which the function reaches half its maximum value.

The term "interferogram" or "Fourier transform spectrum" refers to the detector response as a function of the optical path length difference caused by the interference of electromagnetic radiation.

In the embodiments of this invention, chemical species could be detected remotely by Raman lidar-based instrument using optical signals from electromagnetic radiation including visible light. The instruments of the embodiments of the invention capture Raman signals from a sample resulting from Raman scattering from the sample.

Raman scattering is a powerful light scattering technique used to diagnose the internal structure of molecules and crystals. In a light scattering experiment, light of a known frequency and polarization is emitted from a sample. The scattered light is then analyzed for frequency and polarization. Raman scattered light is frequency-shifted with respect to the excitation frequency, but the magnitude of the shift is independent of the excitation frequency. This "Raman shift" is therefore an intrinsic property of the sample.

Because Raman scattered light changes in frequency, the rule of conservation of energy dictates that some energy is deposited in the sample. A definite Raman shift corresponds to vibrational energy of the sample (i.e. the energy of a free vibration of a molecule). In general, only some vibrational bands of a given molecule are "Raman active," that is, only some may take part in the Raman scattering process. Hence the frequency spectrum of the Raman scattered light maps out part of the vibrational spectrum. Other spectroscopic techniques, such as IR absorption, could be used to map out the non-Raman active excitations.

Additional information, related to the spatial form of the excitation, derives from the polarization dependence of the Raman scattered light. The shape of an excitation in a material, for example a vibration pattern of the atoms in a molecule, and the polarization dependence of the scattering, are determined by the equilibrium structure of the material through the rules of group theory. By this route one gleans valuable and unambiguous structural information from the Raman polarization dependence.

Raman spectroscopy technique of the embodiments of the invention is based upon the Raman effect which may be described as the scattering of light from a gas, liquid or solid with a shift in wavelength from that of the usually monochromatic incident radiation.

Raman spectroscopy provides information about molecular vibrations that can be used for sample identification and quantification. The technique of the embodiments of the invention involves shining a monochromatic light (i.e., laser) on a sample. Laser-produced, monochromatic light of ultraviolet, visible, or infrared frequency could be used as the light source. In some embodiments of the Raman spectroscopy technique of the embodiments of the invention, visible lasers could used (e.g., Ar+, Kr+, Nd:YAG, He—Ne, diode) to create molecular vibration to high-energy "virtual" states of excitation.

The light interacts with the sample and part of it is transmitted, part of it is reflected, and part of it is scattered. The scattered light is detected by one or more detectors. The majority of the scattered light is of the same frequency as the excitation source; this is known as Rayleigh or elastic scattering. A very small amount of the scattered light (less, than 1%, but more likely about $10^{-5}$ of the incident light intensity), called Raman or inelastic scattering, has frequencies different from that of the incident light due to interactions between the incident electromagnetic waves and the vibrational energy levels of the molecules in the sample.

That is, the scattered radiation is examined spectroscopically, not only is light of the exciting frequency, $v_0$, observed (Rayleigh scattering), but also some weaker bands of shifted frequency are detected. Moreover, while most of the shifted bands are of lower frequency $v_0-v_i$, there are some at higher frequency, $v_0+v_i$. By analogy to fluorescence spectrometry, the former are called Stokes bands and the latter anti-Stokes bands. The Stokes and anti-Stokes bands are equally displaced about the Rayleigh band; however, the intensity of the anti-Stokes bands is much weaker than the Stokes bands and they are seldom observed. The scattered radiation produced by the Raman effect contains information about the energies of molecular vibrations and rotations, and these depend on the particular atoms or ions that comprise the molecule, the chemical bonds connect them, the symmetry of their molecule structure, and the physico-chemical environment where they reside.

Plotting the intensity of this "shifted" light versus frequency results in a Raman spectrum of the sample. The Raman spectra could also be plotted as intensity versus the difference in frequency of the incident light and scattered light such that the Rayleigh band lies at $0\,cm^{-1}$ and the Raman band lie on both sides of the Rayleigh band. On this scale, the band positions could lie at frequencies that correspond to the energy levels of different functional group vibrations. The Raman spectrum can thus be interpreted similar to the infrared absorption spectrum.

The vibrational Raman effect is especially useful in studying the structure of the polyatomic molecule. If such a molecule contains N atoms it can be shown that there could be 3N–6 fundamental vibrational modes of motion only (3N–5 if the molecule is a linear one). Those which are accompanied by a change in electric moment can be observed experimentally in the infrared. The remaining ones, if occurring with a change in polarizability, could be observable in the Raman effect. Thus both kinds of spectroscopic measurements could be applied in a complete study of a given molecule.

Like infrared spectrometry, Raman spectrometry is a method of determining modes of molecular motion, especially the vibrations, and their use in analysis is based on the specificity of these vibrations. The methods are predominantly applicable to the qualitative and quantitative analysis of covalently bonded molecules rather than to ionic structures. Nevertheless, they can give information about the lattice structure of ionic molecules in the crystalline state and about the internal covalent structure of complex ions and the ligand structure of coordination compounds both in the solid state and in solution.

Both the Raman and the infrared spectrum yield certain description of the internal vibrational motion of the molecule in terms of the normal vibrations of the constituent atoms. However, IR absorption and Raman scattering are governed by completely different selection rules. Infrared bands arise from an interaction between light and the oscillating dipole moment of a vibrating molecule. Raman bands arise from an oscillation induced dipole caused by light waves interacting with the polarizability ellipsoid of a vibrating molecule. (It is common to describe the polarizability ellipsoid as the shape of the electron cloud around the molecule). Thus, symmetric stretches, vibrations involving multiple bonds, and vibrations of heavier atoms typically give rise to strong bands in the Raman spectrum. Asymmetric molecules could have bands at similar frequencies in both the infrared and Raman spectra, but their relative intensities could be very different. In most cases, a chemical species could have strong, indicative bands in both its Raman and IR spectra but they may not coincide.

Neither Raman nor IR spectra alone might give a complete description of the pattern of molecular vibration, and, by analysis of the difference between the Raman and the infrared spectrum, additional information about the molecular structure can sometimes be inferred. Physical chemists have made extremely effective use of such comparisons in the elucidation of the finer structural details of small symmetrical molecules, such as methane and benzene, but the mathematical techniques of vibrational analysis are not yet sufficiently developed to permit the extension of these differential studies to the Raman and infrared spectra of the more complex molecules that constitute the main body of both organic and inorganic chemistry.

Raman spectra are very specific, and chemical identifications can be performed by using search algorithms against digital databases. As in infrared spectroscopy, band areas are proportional to concentration, making Raman amenable to quantitative analysis. In fact, because Raman bands are inherently sharper than their infrared counterparts, isolated bands are often present in the spectrum for more straightforward quantitative analysis. By the technique of the embodiments of the invention, one can use Raman alone, or in combination with IR spectra, in two ways. At the purely empirical level they provide "fingerprints" of the molecular structure and, as such, permit the qualitative analysis of individual compounds, either by direct comparison of the spectra of the known and unknown materials run consecutively, or by comparison of the spectrum of the unknown compound with catalogs of reference spectra. By comparisons among the spectra of large numbers of compounds of known structure, it has been possible to recognize, at specific positions in the spectrum, bands which can be identified as "characteristic group frequencies" associated with the presence of localized units of molecular structure in the molecule, such as methyl, carbonyl, or hydroxyl groups. Many of these group frequencies differ in the Raman and infrared spectra.

Thus, by the Raman spectroscopy technique of the embodiments of the invention, wavelengths and intensities of the scattered light can be used to identify functional groups of molecules because each compound has its own unique Raman spectrum which can be used as a finger print for identification. It has found wide application in the chemical, polymer, semiconductor, and pharmaceutical industries because of its high information content.

Raman spectra, not only provides a chemical fingerprint, but also provides additional information including:

Identification of minerals and organic substances. From the identities of minerals, we know the chemical formulas and the arrangements of the atoms within them. Thus, we know whether the mineral was a carbonate, sulfate, phosphate, silicate, oxide, sulfide, hydroxide, etc. In some cases for which chemical compositions can vary, e.g., in the ratio of iron to magnesium ions, we can determine the cation ratio Easy sampling of solids, powders, gels, liquids, slurries, and aqueous solutions No sample preparation Sampling through windows, transparent containers, blister packs, or by immersion Remote sampling using fiber optic probes (up to 100 meters)

Sharp spectral peaks for quantitative and qualitative analysis

Identification of phases (mineral inclusions, daughter minerals in fluid inclusions, composition of the gas phase in inclusions)

Anions in the fluid phase ($CO_3^{2-}$, $HCO_3^-$, $PO_4^{3-}$, $BO_4^{3-}$, $SO_4^{2-}$, $HS^-$, $OH^-$)

Identification of crystalline polymorphs (sillimanite, kyanite, andalusite and others)

Measurement of mid-range order in solids

Measurement of orientation

Measurement of stress

High-pressure and high-temperature in situ studies

Phase transition and order-disorder transitions in minerals (quartz, graphite)

Water content of silicate glasses and minerals

Speciation of water in glasses

Raman scattering technique of the embodiments of the invention is a spectroscopic technique that is complementary to infrared absorption spectroscopy. Raman offers several advantages over mid-IR and near-IR spectroscopy, including:

Little or no sample preparation is required

Water is a weak scatterer—no special accessories are needed for measuring aqueous solutions Water and $CO_2$ vapors are very weak scatterers - purging is unnecessary Inexpensive glass sample holders are ideal in most cases Fiber optics (up to 100's of meters in length) can be used for remote analyses Since fundamental modes are measured, Raman bands can be easily related to chemical structure Raman spectra are "cleaner" than mid-IR spectra—Raman bands are narrower, and overtone and combination bands are generally weak The standard spectral range reaches well below 400 $cm^{-1}$, making the technique ideal for both organic and inorganic species Raman spectroscopy can be used to measure bands of symmetric linkages which are weak in an infrared spectrum (e.g. —S—S—, —C—S—, —C=C—)

Raman scattering is, as a rule, much weaker than Rayleigh scattering (in which there is no frequency shift) because the interactions which produce Raman scattering are higher order. Therefore, it is preferred to use an intense source which is as monochromatic as possible—a laser with a narrow linewidth is usually used—and the collected light should be carefully filtered to avoid the potentially overwhelming Rayleigh signal. Other potentially large sources of non-Raman signal include fluorescence (the decay of long-lived electronic excitations) and of course light from ambient sources. Fluorescence can be particularly pernicious to a Raman measurement because the fluorescence signal is also shifted from the laser frequency, and so can be much more difficult to avoid. Note that although the fluorescence spectrum is shifted from the laser frequency, the fluorescence shift depends on the laser frequency whereas the Raman shift does not.

As an analytical technique, Raman spectroscopy has major advantages, the most important being the ease of sample preparation and the rich information content. Raman is essentially a light scattering technique, so all that is required for collection of a spectrum is a means to place the sample into the excitation beam and collecting the scattered light. Therefore in the embodiments of the invention, there are few concerns with sample thickness (as in transmission analyses) and little contribution from the ambient atmosphere, so there is no need for high-vacuum or desiccated sample holders. Glass, water and plastic packaging each have very weak Raman spectra, making the technique easy to use. Often, samples of the embodiments of the invention can be analyzed directly inside the glass bottle or plastic bag without opening the package and risking contamination. Advantageously over infrared spectroscopy, aqueous samples are readily analyzed without the need to remove water, and because ambient humidity is not a problem, there is no need to purge the instrument.

No two molecules would give exactly the same Raman spectrum, and the intensity of the scattered light is related to the amount of material present. This makes it easy to obtain both qualitative and quantitative information about the sample, allowing for spectral interpretation, library searching, data manipulations and the application of quantitative analysis computer methods.

Raman spectroscopy by the embodiment of this invention is generally non-destructive. Unlike IR—or other spectroscopy techniques, there could be no need to dissolve solids, press pellets, compress the sample against optical elements or otherwise alter the structure of the sample in the embodiments of the invention. Raman spectrometers of the embodiments of the invention could employ one of two technologies for the collection of spectra: (1) Dispersive Raman spectroscopy and (2) Fourier transform Raman spectroscopy. Each technique has its unique advantages and is suited to specific analyses. Raman spectroscopy may also be performed on chemical species in the vapor phase without having to chemically fix the species. Some embodiments of the invention also include microscopic examination of the samples using Raman microscopes and Raman confocal microscopes to analyze for texture.

The embodiments of this invention relate to an instrument comprising: (a) an illumination source configured to illuminate a field of illumination on a surface of a substrate that is configured to hold a sample, the field of illumination having (i) an area greater than that of a single spot of light on a surface of a substrate that is configured to hold a sample of a spot scanning Fourier transform spectrometer, (ii) an area greater than that of at least one pad of an array or (iii) a diameter greater than 10 microns, or between 2 to 5 microns, or between 10 to 100 microns, or between 25 to 500 microns; (b) an interferometer; and (c) a detector, wherein the instrument is configured to perform Fourier transform imaging without single spot scanning or without line scanning and the sample emits electromagnetic radiation at one or more wavelengths different from an illumination wavelength of the illumination source. The interferometer could be configured to create a varying phase shift in the electromagnetic radiation emitted from the sample to create an interferogram. Also, the detector could be configured to detect and record the interferogram. The apparatus could further comprise a microprocessor comprising software or a hardware to inverse Fourier transform the interferogram to produce a spectrum.

After passing through the interferometer, the intensity of the electromagnetic radiation could be measured as a function of phase shift. The phase is varied to obtain the Fourier transform of the spectrum. The characteristic could be wavelength, frequency, wave number, amplitude or any other property of the spectrum of electromagnetic radiation (e.g., light).

The illumination source of the embodiment of the invention could comprise a light source and a beam expander. The illumination source could comprise multiple light sources emitting multiple beams. The illumination source could also comprise a single light source that is sufficiently spatially broad to expose an area on the surface of the substrate.

The interferometer of the embodiments of the invention could comprise a beam splitter, a fixed mirror and a movable reference mirror. The distance between the beam splitter and the fixed mirror is generally different from the distance between the beam splitter and the movable reference mirror. The interferometer could comprise a Michelson interferometer, wherein the Michelson interferometer could comprise at least one movable mirror for adjusting an optical path difference. In one variation, the Michelson interferometer could comprise an electro- or thermo-optical material for providing an optical path difference.

In other embodiments of the instrument of the invention, the interferometer could comprise a Mach-Zehnder interferometer. The Mach-Zehnder interferometer could comprise an electro- or thermo-optical material for providing an optical path difference.

In other embodiments of the invention, the Fourier transform imaging comprises Fourier transform imaging of a Raman signal or of a fluorescent signal. The instrument of the embodiments of the invention could be used to analyze a sample comprising a biomolecule, a macromolecule, a nanomaterial, a capture molecule, Raman-active organic compound or a fluorescent compound.

Other embodiments of the invention relates to an instrument comprising: (a) an illumination source configured to illuminate a field of illumination and simultaneously expose multiple pads that emit electromagnetic radiation at one or more wavelengths different from an illumination wavelength of the illumination source, (b) an interferometer configured to create a varying phase shift in the electromagnetic radiation emitted from the multiple pads and create an interferogram, (c) a detector configured to detect the interferogram, and (d) a microprocessor comprising software or a hardware to inverse Fourier transform the interferogram and produce the spectrum, wherein the instrument is configured to perform spatial imaging of the multiple pads without line scanning and without single spot scanning. Preferably, detector has an ability to convert an optical signal of the interferogram to an electrical signal and the electromagnetic radiation comprises light. The instrument could further comprise a beam emitter that emits a beam that strikes the multiple pads, wherein the beam comprises laser. Also, the instrument could further comprise optical elements to collect and concentrate the electromagnetic radiation emitted from the multiple pads.

In one variation of the instrument of the embodiments of the invention, the detector is a single detector and the detector could be a charge coupled device, or an array of photodiodes. Preferably, the electromagnetic radiation emitted from the multiple pads comprises a Raman signal, an infrared (IR) signal, a fluorescence signal, or a luminescence signal.

In one variation of the embodiments of the invention, the interferometer comprises two arms to pass a portion of the electromagnetic radiation emitted from the sample through each of the two arms, wherein preferably one of the two arms comprises a phase shifter comprising a variable index material. Also, in another variation of the embodiments of the invention, the interferometer comprises a MEMS based device, an optical bench, a wafer having optical structures, an optical splitter or an optical waveguide, wherein the optical splitter or the optical waveguide comprises optical fibers coupled to each other to form the optical splitter or the optical guide or the optical bench comprises a MEMS based moving arm.

In one variation of the instrument of the embodiments of the invention, the instrument could comprise a bandpass filter disposed along an optical path of an emitted electromagnetic radiation from the sample for removing electromagnetic radiation generated by the illumination source from being received at the detector, wherein the detector is preferably an array detector comprising a plurality of detectors.

Yet other embodiments of the invention relate to a method of collecting Fourier transform (FT) data, comprising: (a) illuminating a field of illumination in a plane containing a sample that emits an original spectrum of electromagnetic radiation, the field of illumination having (i) an area greater than that of a single spot of light on a surface of a substrate that is configured to hold a sample of a spot scanning Fourier transform spectrometer, (ii) an area greater than that of at least one pad of an array or (iii) a diameter greater than 2 micron, or between 4 to 8 microns, or between 15 to 50 microns, or between 75 to 1000 microns, (b) creating an interferogram from the electromagnetic radiation from the sample, (c) detecting the interferogram, and (d) transforming the interferogram into a spectrum by inverse Fourier transform; wherein the method performs the FT data collection without single spot scanning or without line scanning. Preferably, creating an interferogram from the electromagnetic radiation emitted from the sample comprises creating the phase delay in the electromagnetic radiation emitted from the sample and creating an interferogram from the electromagnetic radiation emitted from the sample is performed by an interferometer. Furthermore, preferably, both creating the phase delay in the electromagnetic radiation emitted from the sample and creating the interferogram from the electromagnetic radiation emitted from the sample is performed by an interferometer. In one variation, the detecting an interferogram is performed by a detector and the transforming the interferogram into a spectrum is performed by a microprocessor.

Other embodiments of the invention relate to a method of collecting Fourier Transform (FT) data with an optical imaging system, comprising: (a) simultaneously exposing to an illumination source multiple pads that emit light at one or more wavelengths different from the illumination wavelength; (b) directing the emitted light from the multiple pads along a predetermined optical path; (c) interferometrically sampling the light emitted from the multiple pads; (d) recording the interferogram; and (e) calculating the spectrum from the interferogram.

Figure 4:
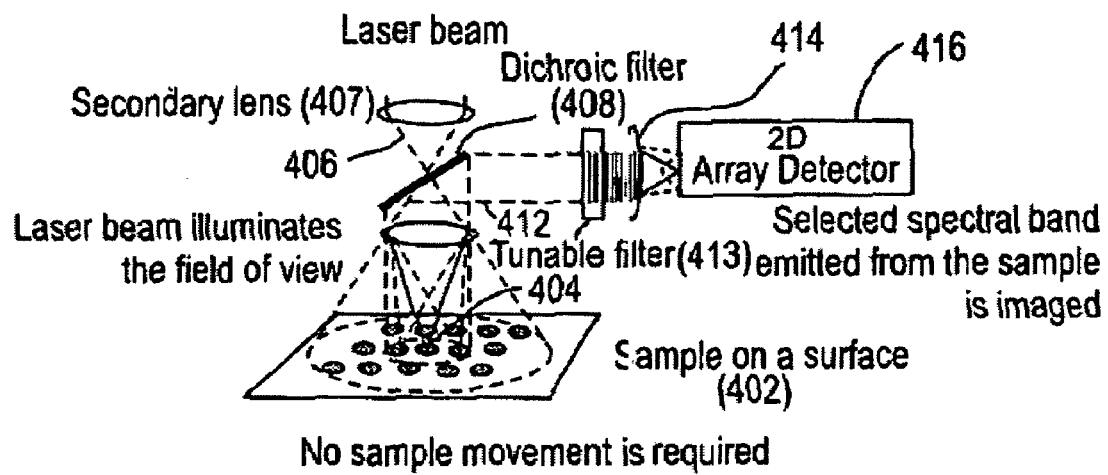
FIG. 4 schematically illustrates a field illumination system that utilizes a tunable filter.

FIG. 4 schematically illustrates a spectral imaging arrangement. A sample 402 is illuminated over a wide area 404, e.g., the entire surface area desired to be imaged. A beam 406 is passed through a secondary lens 407, dichroic filter 408 and lens 410. A two-dimensional emission 412 is collected after passing through lens 410 and reflecting from filter 408. The emission 412 passes through a tunable filter 413, lens 414 and is incident at an array detector 416 that separately detects emissions from multiple points within a two-dimensional sample 402. As indicated, no sample movement is involved if the entire surface area of the sample 402 is illuminated and may be detected at the array detector 416. Of course, multiple areas of a same sample may be imaged separately, in which case a corresponding number of sample movements would be involved. The tunable filter 413 transmits a narrow bandwidth of an entire desired optical spectrum.

Figure 5A:
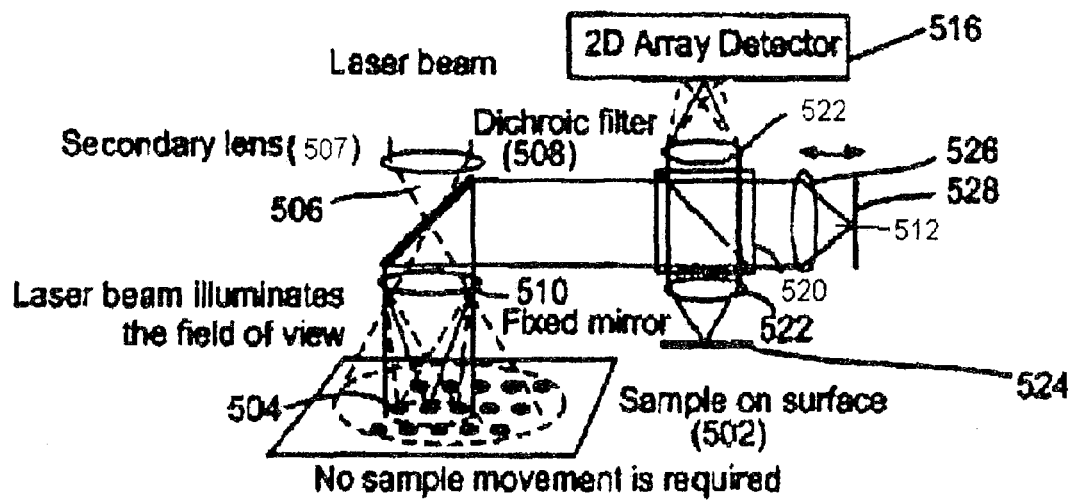
FIGS. 5A-5B schematically illustrate a field illumination FT imaging system in accordance with embodiments of the invention.
Figure 5B:
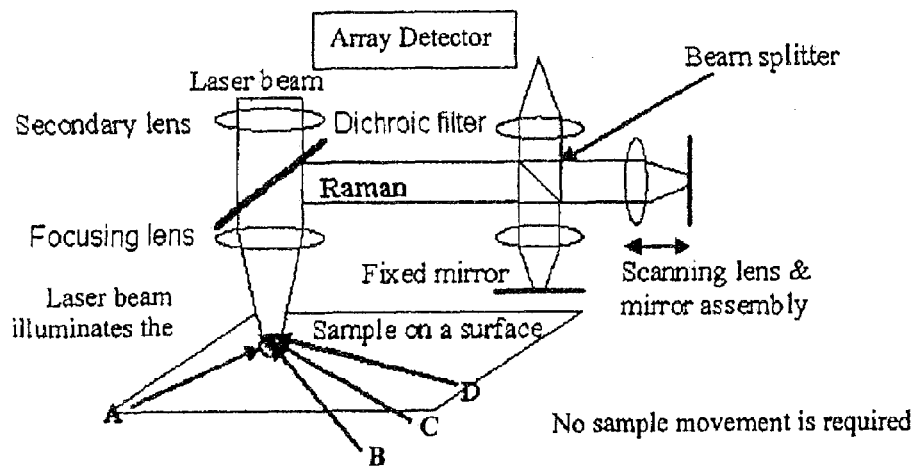

FIGS. 5A-5B schematically illustrate a Fourier-transform (FT) optical imaging system in accordance with embodiments of the invention. The system may be used for Raman imaging, fluorescence imaging or another optical imaging application.

In FIG. 5A, a sample 502 is illuminated over a wide area or field 504 with a narrowband light beam 506 (e.g., a laser beam or an emission from a porous silicon optical cavity). The sample 502 may be a biological sample.

Figure 12:
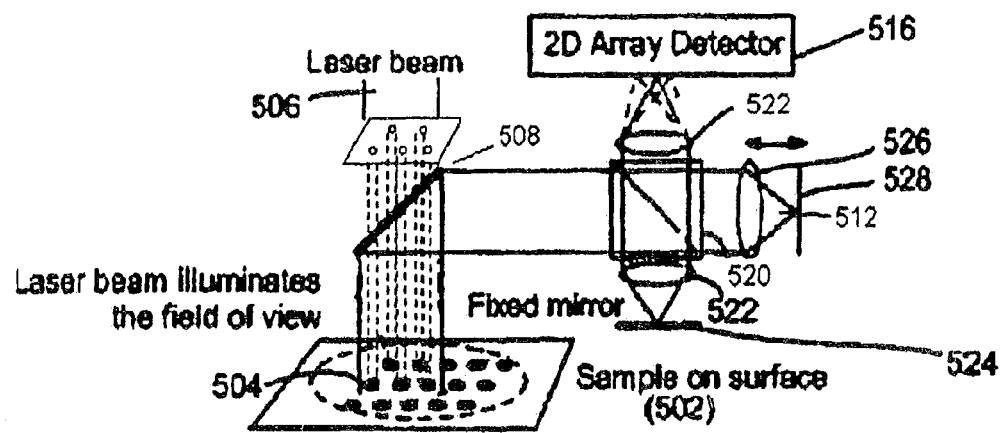
FIG. 12 schematically illustrate a field illumination FT imaging system in accordance with embodiments of the invention.

This type of illumination is known as field illumination. In field-illumination, the excitation light is intentionally broadened spatially to a larger area than is illuminated in a spot scanning method. Preferably, field-illumination is achieved with secondary lens 507, which defocuses the light at the focal plane of the focusing lens 510. Alternatively, multiple beams are generated by multiple light sources each illuminating a different sample spot to be independently detected at the array detector 516. In another alternative embodiment, illustrated in FIG. 12, a beam of light from a single light source may be split to provide multiple beams.

After secondary lens 507, the illumination beam 506 transmits dichroic filter 508 and is incident onto the sample plane 502 after transmitting focusing lens 510. A two-dimensional emission 512 is collected from the sample 502 after transmitting the lens 510 and reflecting from the filter 508. The dichroic filter 508 generally reflects the Raman scattered light or other sample emission 512, while transmitting the illumination light 506. The reverse configuration of a dichroic filter 508 is also possible (i.e., the filter 508 may reflect the illumination light 506, while transmitting the Raman scattered light or other optical emission 512).

The emission 512 is then incident at an interferometer 513 and array detector 516. In FIG. 5A, a Michelson interferometer is illustrated. The array detector 516 detects interference spectra from multiple points over the two-dimensional area of the sample 502 that is being measured. If the sample is field-illuminated, a generated interferogram maintains spatial information of the sample. Thus, by using an array detector 516, the interferogram can be recorded into an image format.

According to the Michelson interferometer of FIG. 5A, an optical signal 512 is incident at a 50:50 beam splitter 520. The 50:50 beam splitter 520 splits the signal 512 into two paths: one through lens 522 toward a fixed mirror 524, and the other through lens 526 toward a moving (scanning) mirror 528. The lenses 522 and 526 of FIG. 5A before the fixed and moving mirrors 524 and 528, respectively, are preferred, but may be removed in an alternative system. The lenses 522 and 526 should be placed at the focal length distance from the mirrors 524 and 528, respectively. This focuses the light onto a tight spot, and permits use of smaller-sized mirrors. In turn, the tight spots produced and incident at mirrors 524 and 528 reduce flatness requirements for the mirrors 524 and 528.

The split-off portions of the optical emission 512 reflect from the respective mirrors 524 and 528 and propagate back toward the beam splitter 520. The two portions of the sample emission 512 are then merged by the beam splitter 520. The merged light generates an interferogram due to an optical path length difference in travel.

The moving mirror 528 (and lens 526) can be positioned in a linear scanning pattern or in a step-wise scanning pattern to create interferograms. By scanning the moving mirror 528, interferograms for desired path length differences can be obtained. An automated mechanical alignment of the moving mirror 528 may be used, as the performance of the interferometric spectrometer may be significantly affected by misalignment. Alternatively, software can be used to compensate for misalignment during scanning.

The embodiment of FIG. 5B is functionally similar to the embodiment of FIG. 5A expect that the illuminating laser beam illuminates a field of illumination having a diameter greater than 10 microns (instead of multiple pads of an array as in FIG. 5A), which includes several submicron diameter points A, B, C and D, for example. A conventional single spot spectrometer would have required individual FT Raman scans at each one of the several submicron diameter points, resulting in many scans to process a sample size of greater than 10 microns. On the other hand, the FT spectrometer of FIG. 5B could obtain the spectral data of the sample over a view of view having a diameter greater than 10 microns by a single scan, for example.

Figure 9:
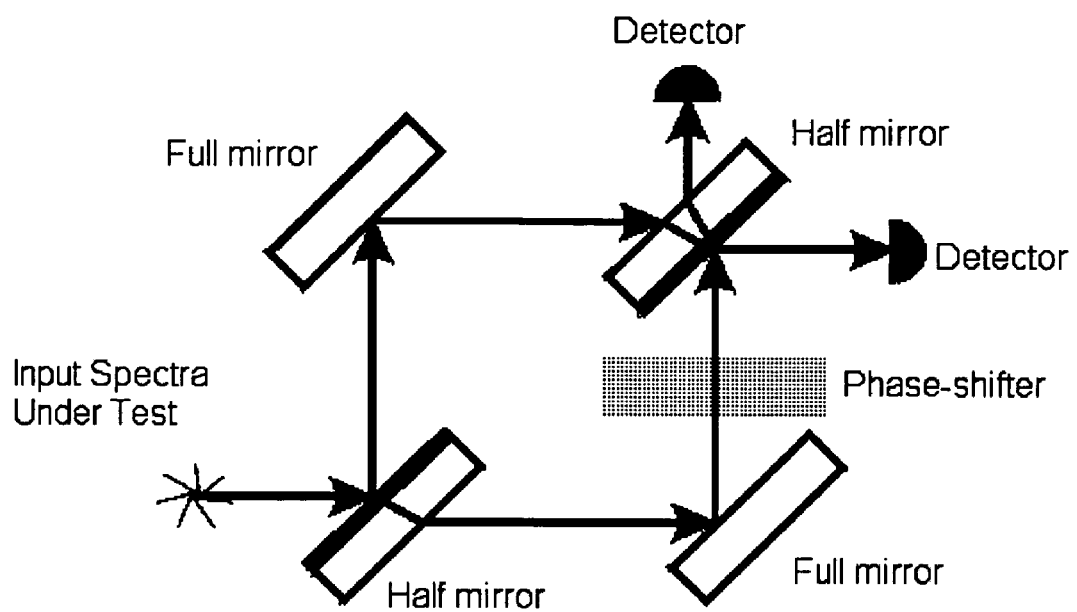
FIG. 9 schematically illustrates an interferometer of embodiments of this invention.

Alternatively, a Mach-Zehnder interferometer such as that shown in FIG. 9 or another interferometer can be used instead of the described Michelson interferometer 513. In alternative approaches with either of these interferometer types, electro-optical or thermo-optical materials may be used to create optical path length differences (OPL), which equals refractive index times distance, instead of moving the mirror 528. The desired electro-optical or thermo-optical material should have a varying index of refraction under different electromagnetic fields or temperatures.

An interferogram collected for each sample spot is mathematically equivalent to the Fourier Transformation of the optical spectrum (e.g. Raman and/or fluorescence) emitted from the sample spot. Numerical computations can be performed to obtain the optical spectrum or characteristic pattern of the optical spectrum from the interferogram.

A Mach-Zehnder interferometer shown in FIG. 9 is functionally similar to the Michelson-type beam splitting interferometer of FIG. 5A. However, instead of creating the phase delay by changing the path length difference as in the Michelson interferometer, in Mach-Zehnder interferometer (MZI) a variable index-of-refraction material could be put into one of the two beam paths. By carefully controlling the index-of-refraction of the material, different interference fringes could be formed, which can be recorded by a single channel detector, for example. The recorded signal could be computed (inverse Fourier transformed) by a microprocessor to obtain the spectrum. The above embodiments of the instrument would not require a spectrometer having a dispersive grating or having any moving parts.

An alternative embodiment could be a miniaturized Michelson interferometer with a micro-electro-mechanical-system (MEMS) based moving arm. Multiple folded mirrors can be used to increase the path length difference. Optionally, separated waveguides with a reference light source may pass through the same phase-shifter to monitor the phase shifting accurately.

In one embodiment of the instrument of the invention, a beam emitted from a beam emitter, e.g. an Argon-ion laser, could be filtered for monochromaticity and directed by a system of mirrors to a focusing/collecting lens. The beam could be focused onto the sample and the scattered light from the sample could be allowed to passes through a set of lens into a first stage of the instrument. Preferably, the sample should be oriented such that the specular reflection from the sample passes outside of the collection lens-therwise, the reflection of the beam striking the sample could potentially damage the detector, which could be designed to be sensitive enough to even detect weak Raman signals emitted by the sample.

The instrument of the embodiments of the invention could generally be separated into four stages. The first stage could include optical elements (collecting lenses, for example) to collect and concentrate the electromagnetic radiation emitted from the sample.

In one embodiment, the second stage is an interferometer comprising optical waveguides having at least two arms, for example, with input and output focusing mirrors. The incoming signal from the collecting lenses could be passed through a first pair of arms of the optical waveguide, wherein a variable index-of-refraction material could be put into one of the two beam paths of the first pair of arms of the optical waveguide. By carefully controlling the index-of refraction of the material a varying phase shift could be introduced into one of the arms of the MZI and different interference fringes could be formed at the output of the interferometer. This light can be refocused and the light contains information in the form of the Fourier transform of the spectrum of light emitted by the sample.

This refocused light is sent out to the third stage, which is the detector, preferably an array detector. The detector converts the interferogram to an electrical signal. The detector could be a charge coupled device, or an array of photodiodes.

The phase/intensity information as electrical signals generated by the detector is then read to a microprocessor, which is the fourth stage of the instrument. The microprocessor contains software or a hardware to inverse Fourier transform the interferogram into the spectrum of light emitted by the sample, which could be a frequency/intensity or wavelength/intensity spectrum such as a Raman spectrum, for example.

The data from the microprocessor could come out as an intensity/frequency plot of a spectrum. To resolve a peak of a certain width of the spectrum, the resolution of the instrument could be smaller than the peak width.

As the instrument in its parts or as a whole could have a wavelength (or frequency) dependent transmittance, the actual spectrum displayed is a product of the spectrometer frequency response with the actual spectrum of the scattered light. Thus, to know not only the energies of particular excitations, for example, Raman-active excitations, but also the relative magnitudes of the scattering at different frequencies, it would be desirable to calibrate the instrument response to a source with a known spectrum. Thus, one could use a traceable standard lamp or a spectrum from a well-characterized piece of luminescent glass.

The embodiments of the instrument of this invention could be directed, for example by passing through a filter such as an optical filter, to substantially exclude IR signals and include substantially only Raman signals, for example, that are detected by a detector. This filter can be integrated directly with the MZI being used as the Fourier transform spectrometer. As an example of such a filter, notch filters can be fabricated by etching a surface corrugation onto a silicon waveguide, these filters are commonly called Bragg filters. By cascading multiple filters together high pass and low pass filters may be formed which could optimize the signal to noise of the entire system. Other examples of filter types include ring resonators, etalons or MZI interferometers.

The instrument of the embodiments of the invention could further include an edge filter, which could be located prior to the interferometer or between the interferometer and the detector. The edge filter of the embodiments of the invention could be of long or short wave pass types produced by established multi-layer thin film coating techniques from all-dielectric materials. This manufacturing method allows a high degree of flexibility in edge position coupled with low absorption losses to be achieved, compared with bulk glass or dye filter types. Edges for long and short wave pass types can be set anywhere in the 400 nm to 5000 nm wavelength range. The filter wavelength, regardless of type, is generally specified as the 5% transmission point. Tolerances on this position are generally held to better than +/−2% of cut-on/off wavelength (which are defined at the 5% transmission), although this may be improved by selection. In a long wave pass type edge filter, light of lower wavelength is blocked while light of higher wavelength is transmitted through the edge filter. In a short wave pass type edge filter, light of higher wavelength is blocked while light of lower wavelength is transmitted through the edge filter. The rate of change of transmission of the edge could be approximately 5%. This is generally sufficient for most applications, although steeper edges, tending towards 2% or less, can be produced and may be preferable. Suppression of unwanted transmission 'leaks' outside the pass band could be generally better than <0.1% for the edge filters of the embodiments of the invention. Rejection levels of 0.01% or more can be achieved by the embodiments of the invention. This level of blocking performance, coupled with high average transmissions, could ensure excellent system signal to noise ratios.

A wide range of substrate materials and sizes could be used for the substrate of the edge filter. Some possible sizes of the edge filter include as 12.5 mm, 22 mm and 25 mm diameter. The edge filter can generally be operated in a temperature range of 50° C. to 100° C.

Figure 6A:
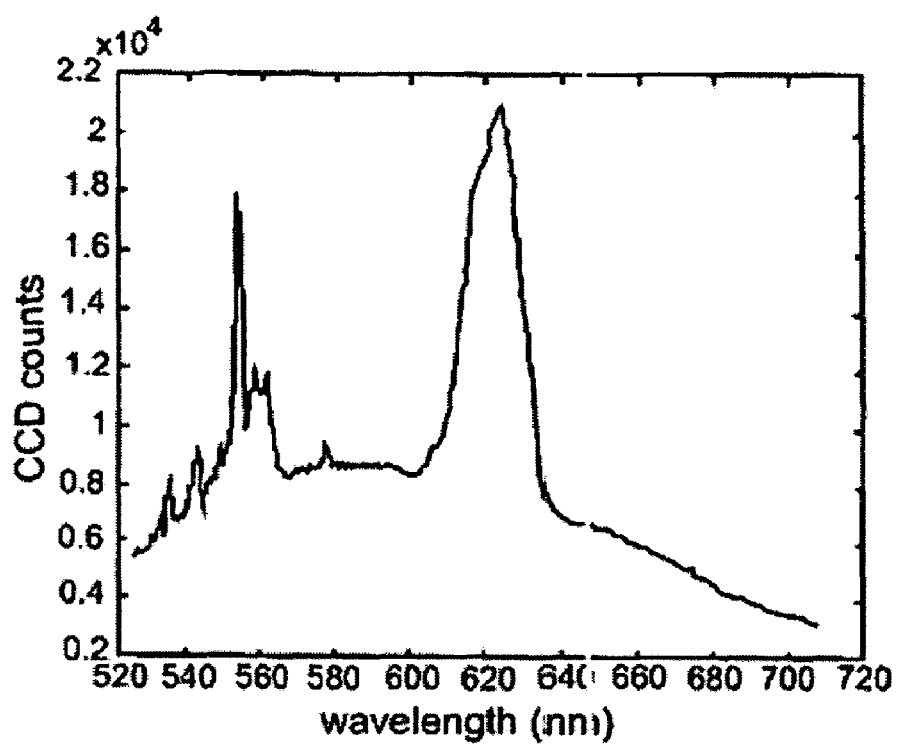
FIGS. 6A-6C are plots of Raman data obtained with the system of FIGS. 5A-5B.
Figure 6B:
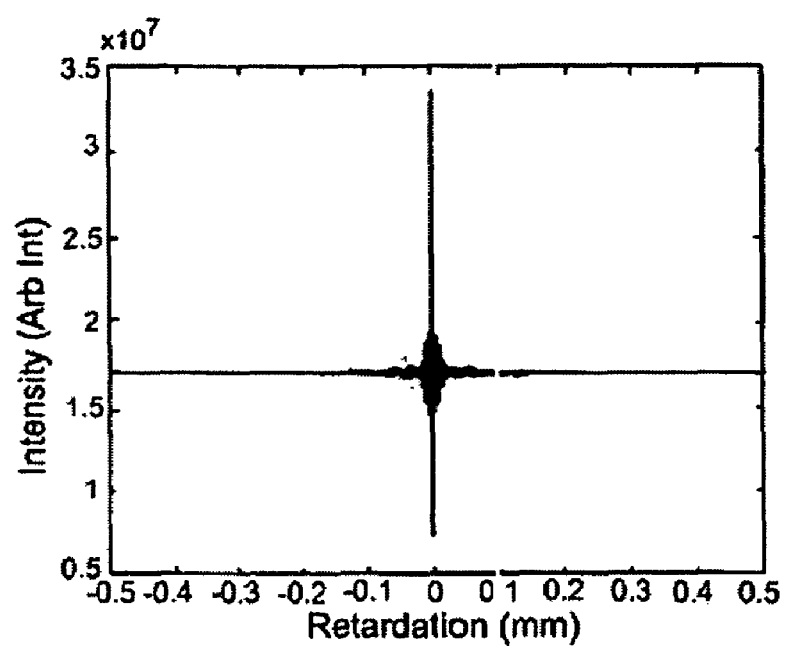
Figure 6C:
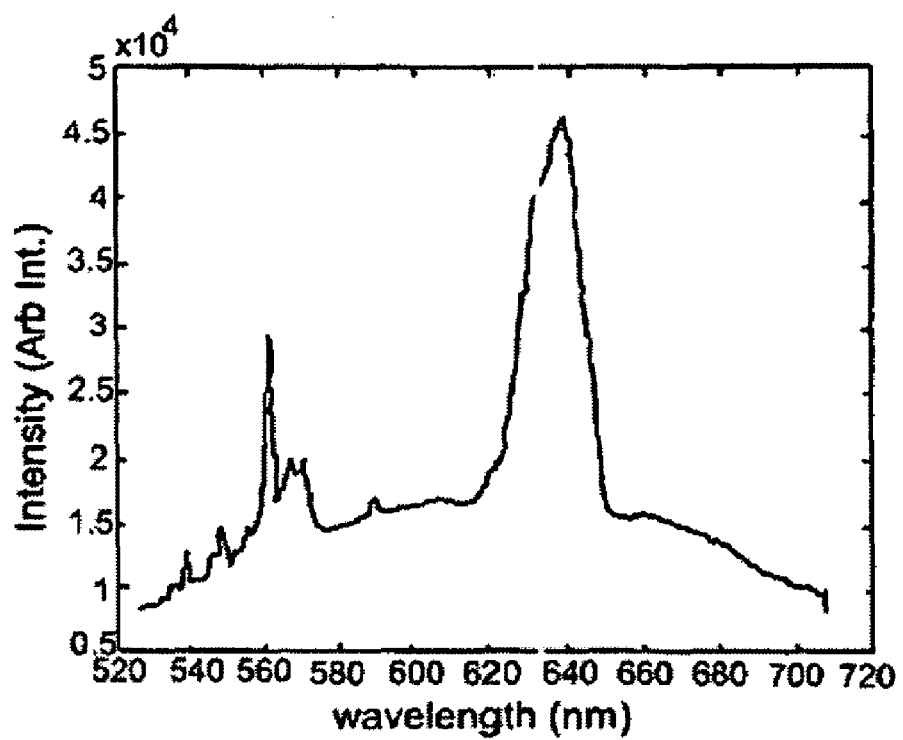

FIGS. 6A-6C show an exemplary Raman spectrum (FIG. 6A) and interferogram (FIG. 6B) simulated by providing different optical path length differences. The Raman spectrum of FIG. 6A is plotted on a wavelength scale for the purpose of this description to illustrate the concept of a Fourier transform spectrometer, although Raman spectra are ordinarily plotted on a wavenumber scale. The excitation laser wavelength was 514 nm.

The interferogram of FIG. 6B is equivalent to the Fourier-transformation of the original Raman spectrum of FIG. 6A. Thus, by computing an inverse Fourier-transform of the interferogram of FIG. 6B, the original Raman spectrum can be obtained as illustrated at FIG. 6C. In real measurements, we would not actually measure the original spectrum of FIG. 6A. What is measured is the data of FIG. 6B (from instrument measurements) and then the plot of FIG. 6C is generated (from computational inverse FT processing).

The system of the preferred embodiment provides real-time imaging, and therefore uses high-grade computer processing equipment. The computer used can process 18 million inverse Fourier transformations of 2,000 data points every second (18 million per second=640 ×480 pixels at 60 frames per second).

Further numerical computation can be performed to identify or classify the obtained spectrum. For example, the intensities of spectral features shown in the optical spectrum or their spectral line shapes can be used for classification by using methods such as univariate intensity measurement, curve fitting, principal component analysis, regression fitting, or another multivariate analysis method. The classified spectrum can be converted to an indicator value, which represents the type of the spectrum and/or the intensity of the spectrum. The indicator value can be plotted to form an image. A pseudo-color may be used to assist the analysis of the image.

Figure 7A:
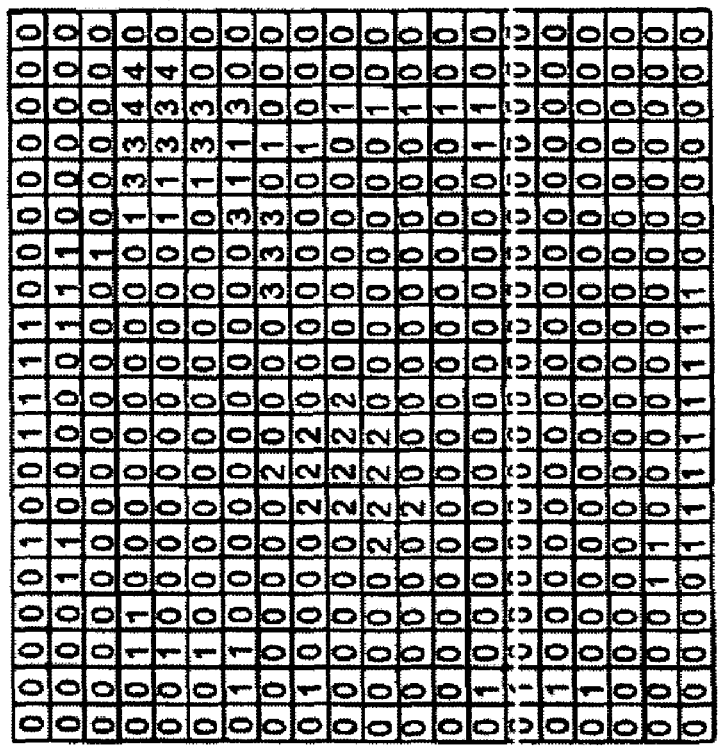
FIGS. 7A-7B schematically illustrate a hypothetical image collected by a field illumination FT imaging system.
Figure 7A:
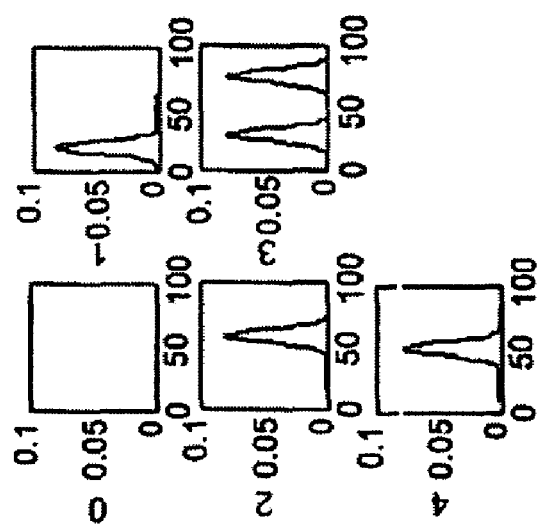
Figure 7B:
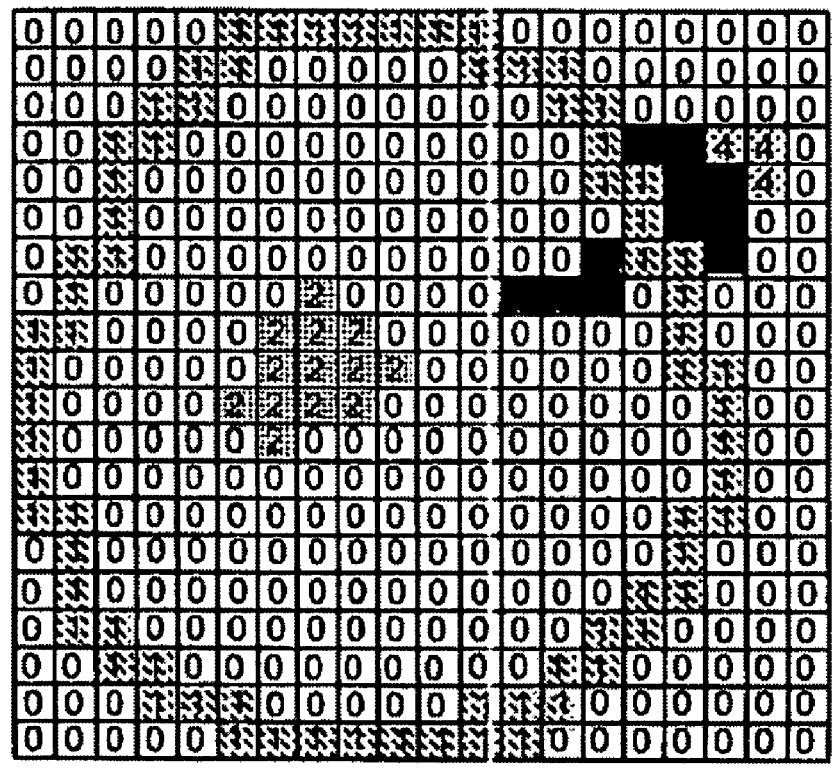
Figure 7B:

FIGS. 7A-7B show a schematic image of a biological sample, which includes 400 spots in a 20×20 array format. An interferogram from each spot was converted to a Raman spectrum by inverse Fourier transformation, and the Raman spectrum was further classified into four categories. For each category, an indicator number was assigned ranging from 1 to 4. Then, the image of the sample was drawn using the indicator number, by utilizing an appropriate color scheme.

In another alternative embodiment, a bandpass filter can be placed between the dichroic filter 508 and the beam splitter 520 of the exemplary system illustrated at FIG. 5A. The bandpass filter may be used to reduce contributions from the illumination light source at the detector 516. In another embodiment, the bandpass filter may be used to select the wavelength range of spectrum that contains most relevant information for each sample.

Figure 8A:
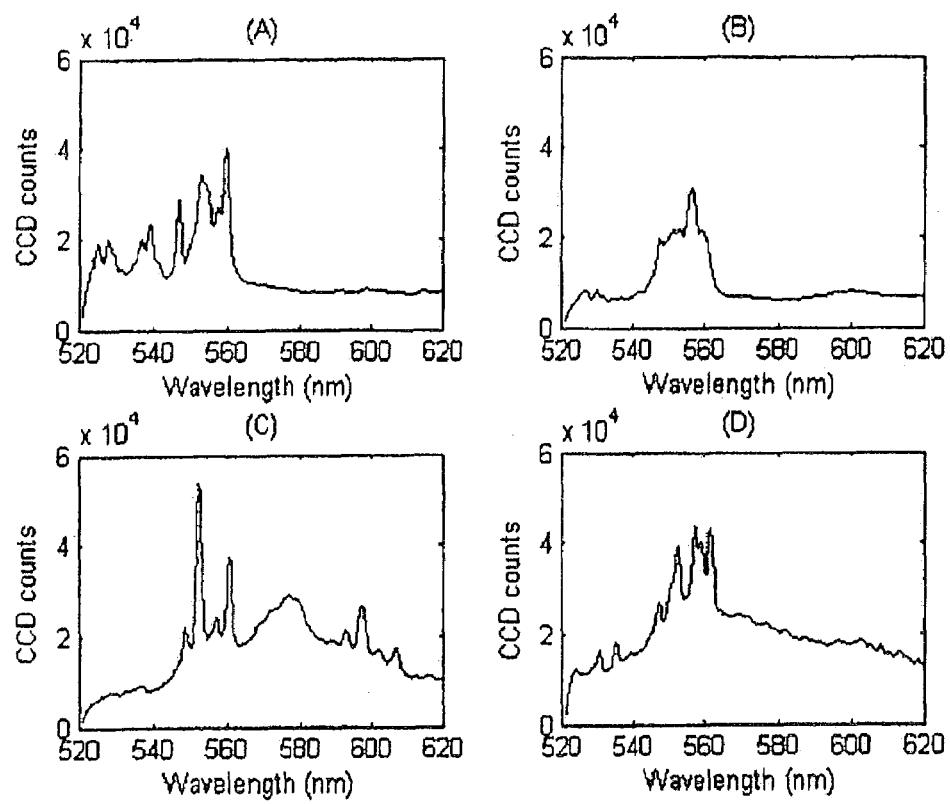
FIG. 8A-8D schematically illustrate a hypothetical image collected by a field illumination FT imaging system illuminating four different parts of a sample.
Figure 8B:
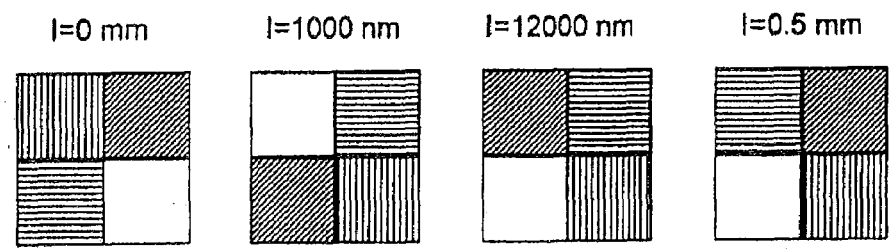

FIGS. 8A-8D schematically illustrate a hypothetical image collected by a field illumination FT imaging system illuminating four different parts of a sample to illustrate the operation of the embodiments of this invention. FIG. 8A shows an exemplary Raman spectra collected from four different parts of a sample, e.g., points A, B, C and D of the sample in FIG. 5B. FIG. 8A is plotted on wavelength scale. However, note that Raman spectrum is usually plotted on wavenumber scale. The excitation laser wavelength was 514 nm. FIG. 8B shows intensity of light collected by an array detector with 4 pixels (2 by 2) by providing different optical path length differences between the moveable reference mirror and fixed mirror. Each pixel corresponds to different location on the sample (e.g. spots A, B, C, and D in FIG. 5B). Intensity was simulated from the exemplary Raman spectra of FIG. 8A.

Figure 8C:
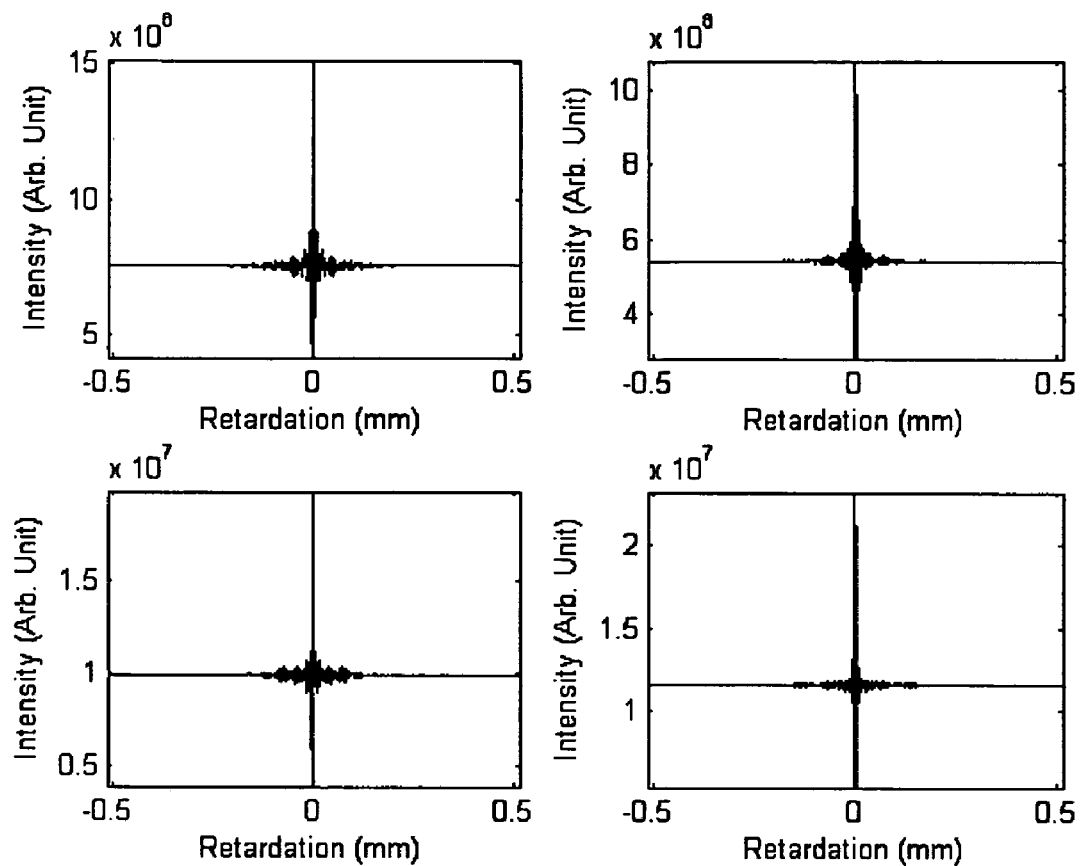
Figure 8D:
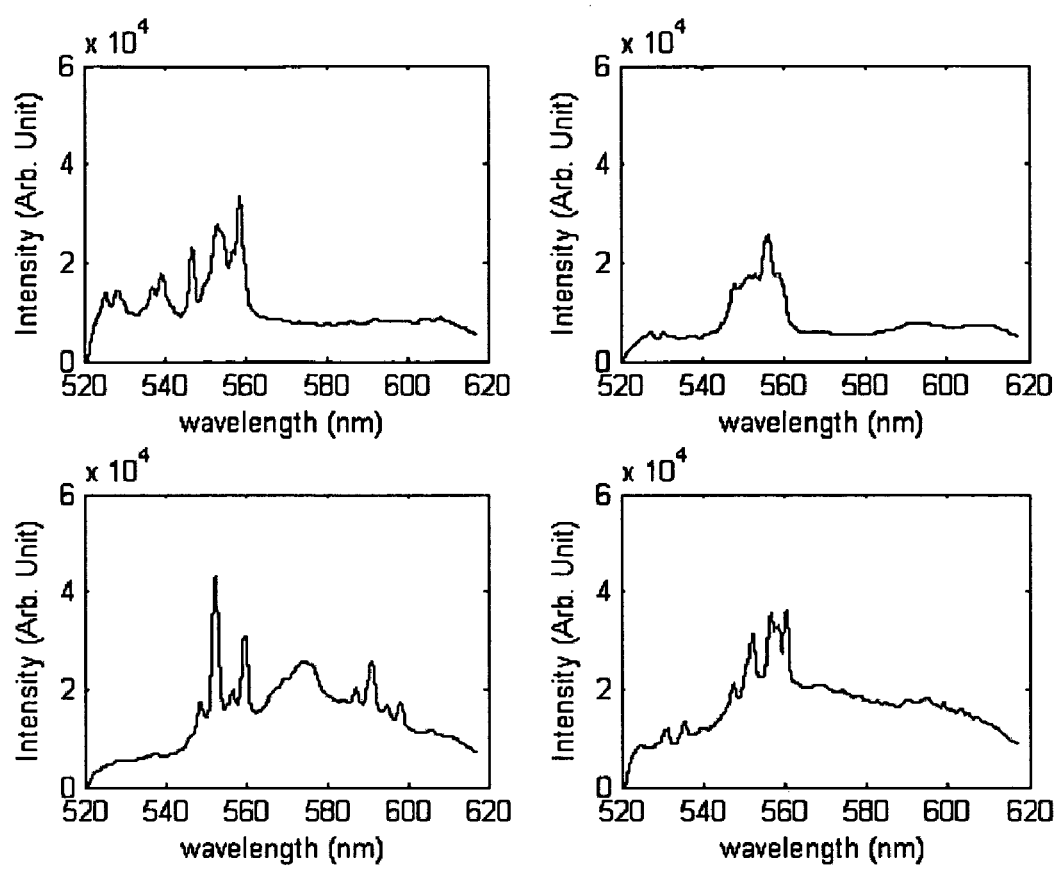

FIG. 8C is similar to FIG. 8B, wherein the interferograms were obtained for a total number of data points of 2048 by providing different optical path length differences between the moveable reference mirror and fixed mirror in fine steps from −0.5 mm to 0.5 mm to create a total optical path length difference of 1 mm. The interferograms were simulated from the exemplary Raman spectra in FIG. 8A, with the optical path length difference between two adjacent sample points being 500 nm. FIG. 8D shows the spectra by inverse Fourier-transformation of the interferograms of FIG. 8C. FIG. 8D shows that all of the major features in the original Raman spectrum of FIG. 8A were reconstructed in FIG. 8D.

The equation of intensity of light from each point (e.g., A, B, C and D in FIG. 5B) after Fourier transform by the Raman imaging system is defined by:

$$I(x, y, l) = \int S(x, y, \lambda) \cdot \left(1 + \cos\left(\frac{2\pi}{\lambda}l\right)\right) \cdot d\lambda,$$

where I is the intensity of light measured by an element of the array detector, corresponding to a location on the sample having coordinates (x,y) when the path length difference or retardation is l; S is the intensity of light originating from a location on the sample having coordinates (x,y) for the wavelength λ. By performing inverse Fourier-transform on I(x,y,l) over the path length difference l, a Raman spectrum in as a function of the wavelength can be obtained.

Fabrication of Fourier-Transform Raman Imager

A non-limiting embodiment of the Fourier-Transform Raman imager includes an interferometer like a Michelson interferometer. A basic Michelson interferometer consists of a beam splitter and two mirrors; the first mirror is fixed in position, while the second is typically mounted on a motorized stage to allow movement along the optical axis. The beam path between the beam splitter and the fixed mirror is often called "the fixed arm" or "the reference arm," while the beam path between the beam splitter and the moving mirror is often called "the moving arm" or "the measuring arm". The preferred beam splitter is a 50/50 non-polarizing beam splitter, which transmits 50% of the incoming light and reflects 50% of the incoming light, regardless of the polarization of the incoming light. The transmitted light can be used for the reference arm and the reflected light can be used for the measuring arm, or vice versa.

In the reference arm, the light coming from the beam splitter propagates toward a fixed mirror, gets reflected by the fixed mirror, and propagates back toward the beam splitter. In the measuring arm, the light coming from the beam splitter propagates toward a mirror mounted on a motorized stage, gets reflected by the mirror, and propagates back toward the beam splitter. The light from the reference arm and the measuring arm, either transmits through or gets reflected by the beam splitter and merges, which creates an interferogram as the merged light propagates toward an array detector through a lens. The lens should be placed from the array detector at a distance equal to the focal length of the lens.

In an alternative embodiment, lenses can be placed between the beam splitter and the mirrors, in order to minimize image distortion by the irregularity of the mirror surface. Preferably the distance between each lens and each mirror should be equal to the focal length of the lens.

In another alternative embodiment, i.e., FT Raman Imager with the Mach-Zehnder Interferometer of FIG. 9, the path length difference or retardation difference can be obtained by using a variable index of refraction material and introducing changes in the index of refraction instead of using a motorized stage.

Fabrication of Mach-Zehnder Interferometer

Figure 10:
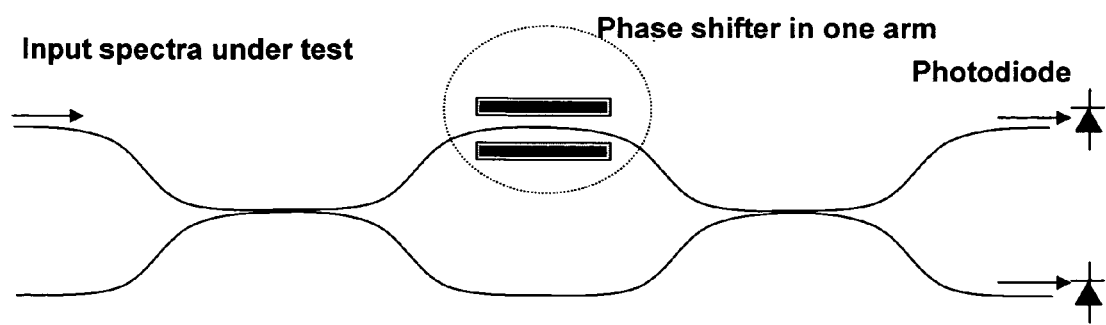
FIG. 10 schematically illustrates a Mach-Zehnder interferometer.

The Mach-Zehnder interferometer such as that shown in FIG. 10 can be fabricated using common semi-conductor fabrication techniques. As an example a silicon wafer could be used as the starting material. An oxide layer could be grown to be used as the bottom cladding of the waveguide. SiON could then be deposited to be used as the waveguide core. This could then have waveguides patterned onto it using wet or dry chemical etching. Control of the index of the MZI arms could be done using the thermo-optic effect by preferentially heating the MZI arms with heaters deposited onto the waveguide. Filters could be integrated onto the waveguide by etching the upper surface or sidewall of the waveguide, or by varying the refractive-index of the waveguide as a function of position. An integrated photo-detector could be formed by fabricated a silicon PIN diode on the same substrate as the spectrometer in a way similar to obtaining planar optical devices that is known to persons of ordinary skill in this art.

Fabrication of Multiple Mach-Zehnder Interferometers with Array Detector

Figure 11:
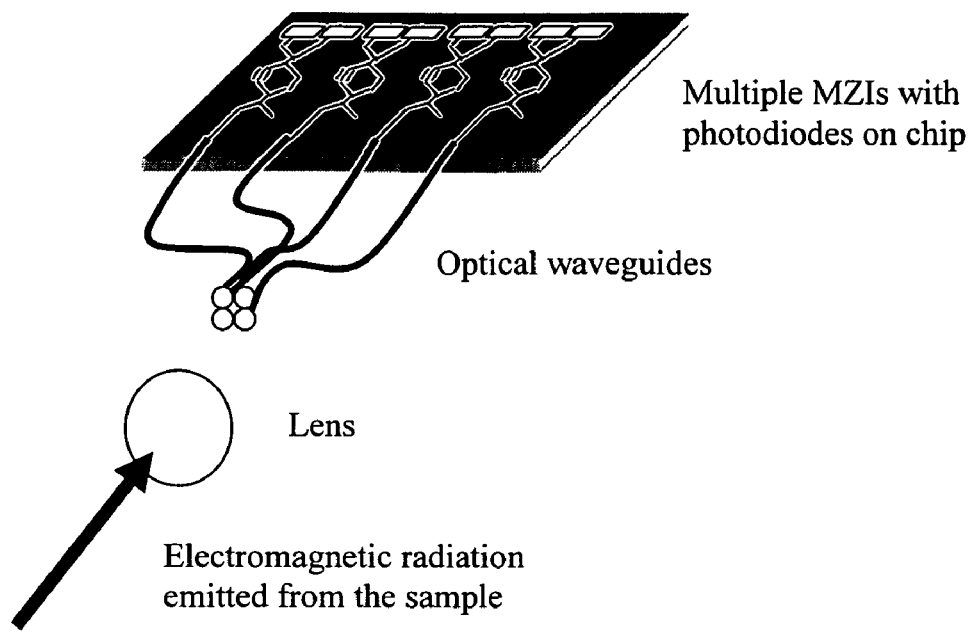
FIG. 11 schematically illustrates multiple Mach-Zehnder interferometers with an array detector.

Multiple Mach-Zehnder interferometers could be combined into an multiple MZIs with photodiodes on a chip as shown in FIG. 11. At one end, each or some of the MZIs of the multiple MZIs could be connected to fiber optic cables which deliver electromagnetic radiation such as light to the MZI. At the other end, each or some of the MZIs of the multiple MZIs could be connected to an array detector having a plurality of detectors or a single detector having multiple channels. Each channel could be for detecting electromagnetic radiation such as light arriving from different location or for detecting electromagnetic radiation such as light having different characteristics such as different wavelengths.

The embodiments of the invention could further include a sample collection device for collecting the sample that has to be analyzed by the instrument of the embodiments of the invention. The sample collection device could include suction and sample concentration devices. For example, a solid, liquid or gaseous sample could be sucked into a sample collection device that produces a known background signal. Then, the sample could be concentrated within the sample collection device. For example, a gas could be cooled to create condensate in the sample collection device. By concentrating the sample in the sample collection device, it could reduce the analysis time, particularly for a gaseous sample.

While only certain features of the invention have been illustrated and described herein, many modifications and changes will occur to those skilled in the art. It is, therefore, to be understood that the appended claims are intended to cover all such modifications and changes as fall within the true spirit of the invention.

The instrument could also be used for therapeutic materials development, i.e., for drug development and for biomaterial studies, as well as for biomedical research, analytical chemistry, high throughput compound screening, and bioprocess monitoring. Yet other applications of the instrument could be for developing new materials, particularly nanomaterials for many purposes including, but not limited to corrosion resistance, battery energy storage, electroplating, low voltage phosphorescence, bone graft compatibility, resisting fouling by marine organisms, superconductivity, epitaxial lattice matching, or chemical catalysis.

It is further contemplated that instrument of the embodiments of the invention could be used to develop screening methods for testing materials. That is, reagents electrochemically generated by an electrode on a die could be used to test the physical and chemical properties of materials. For example, the instrument could be used for testing corrosion resistance, electroplating efficiency, chemical kinetics, superconductivity, electro-chemiluminescence and catalyst lifetimes.

The embodiments of this invention have yet other several practical uses. For example, one embodiment of the invention allows molecules and nanomaterials detection/analysis based on the electrical readout of specific captured Raman signals (fingerprints) of molecules and nanomaterials. Another embodiment of the invention has potential applications for nanomaterials study to be used in electronic devices (transistors and interconnects) as well as well as for detection of bio-species (DNA, protein, viruses etc.) for molecular diagnostics, homeland security, drug discovery and life science R&D work.

This application discloses several numerical range limitations that support any range within the disclosed numerical ranges even though a precise range limitation is not stated verbatim in the specification because the embodiments of the invention could be practiced throughout the disclosed numerical ranges. Finally, the entire disclosure of the patents and publications referred in this application, if any, are hereby incorporated herein in entirety by reference.

The invention claimed is:

1. An instrument comprising:
    an illumination source configured to illuminate a field of illumination on a surface of a substrate that is configured to hold a sample, the field of illumination having a diameter greater than 1 microns,
    a secondary lens configured to defocus light from the illumination source,
    an interferometer, and
    a detector, wherein the detector is an array detector comprising a plurality of detectors or a single detector having multiple channels,
    further wherein the instrument is configured to perform Fourier transform imaging without single spot scanning or without line scanning.

2. The instrument of claim 1, wherein the sample emits electromagnetic radiation at one or more wavelengths different from an illumination wavelength of the illumination source.

3. The instrument of claim 2, wherein the sample emits electromagnetic radiation by Raman scattering.

4. The instrument of claim 1, wherein the interferometer is configured to create a varying phase shift in an electromagnetic spectrum and to create an interferogram.

5. The instrument of claim 1, wherein the detector is configured to detect an interferogram.

6. The instrument of claim 5, further comprising a microprocessor comprising software or a hardware to inverse Fourier transform the interferogram.

7. The instrument of claim 1, wherein the illumination source comprises a light source and a beam expander.

8. The instrument of claim 1, wherein the illumination source comprises multiple light sources emitting multiple beams.

9. The instrument of claim 1, wherein the illumination source comprises a single light source that is sufficiently spatially broad to expose an area on the surface of the substrate.

10. The instrument of claim 1, wherein the spectral bandwidth of the illumination source is narrower than 1 nm full-width at half-maximum.

11. The instrument of claim 1, wherein the interferometer comprises a beam splitter, a fixed mirror and a movable reference mirror.

12. The instrument of claim 1, further comprising a Bragg filter that substantially excludes JR signals and substantially passes Raman signals to the detector.

13. An instrument comprising:
an illumination source configured to illuminate a field of illumination on a surface of a substrate that is configured to hold a sample, the sample comprising an array of pads, the field of illumination having an area greater than that of at least one pad of the array of pads,
a secondary lens configured to defocus light from the illumination source,
an interferometer; and
a detector, wherein the detector is an array detector comprising a plurality of detectors or a single detector having multiple channels, and
further wherein the instrument is configured to perform Fourier transform imaging without single spot scanning or without line scanning.

14. The instrument of claim 13, further comprising a Bragg filter that substantially excludes JR signals and substantially passes Raman signals to the detector.

15. The instrument of claim 13, wherein the interferometer comprises an electro- or thermo-optical material for providing an optical path difference.

16. The instrument of claim 13, wherein the Fourier transform imaging comprises Fourier transform imaging of a Raman signal.

17. The instrument of claim 13, wherein the Fourier transform imaging comprises Fourier transform imaging of a fluorescent signal.

18. The instrument of claim 13, wherein the sample comprise a biomolecule, a macromolecule, a nanomaterial, a capture molecule, Raman-active organic compound or a fluorescent compound.

19. The instrument of claim 13, further comprising a bandpass filter disposed along an optical path of an emitted electromagnetic radiation from the sample for removing electromagnetic radiation generated by the illumination source from being received at the detector.

20. The instrument of claim 13, wherein
the illumination source is configured to illuminate a field of illumination and simultaneously expose multiple pads that emit electromagnetic radiation at one or more wavelengths different from an illumination Wavelength of the illumination source,
the interferometer is configured to create a varying phase shift in an electromagnetic spectrum and to create an interferogram from an original spectrum of the electromagnetic radiation emitted from the multiple pads and Fourier transform the original spectrum to a Fourier transformed spectrum,
the detector is configured to detect the interference patterns, and further comprising
a microprocessor comprising software or a hardware to inverse transform the Fourier transformed spectrum and reproduce the original spectrum,
wherein the instrument is configured to perform spatial imaging of the multiple pads without line scanning and without single spot scanning.

21. The instrument of claim 20, wherein detector converts the interferogram to an electrical signal.

22. The instrument of claim 20, wherein the electromagnetic radiation comprises light.

23. The instrument of claim 20, further comprising a beam emitter that emits a beam that strikes the multiple pads.

24. The instrument of claim 23, wherein the beam comprises laser.

25. The instrument of claim 20, further comprising optical elements to collect and concentrate the electromagnetic radiation emitted from the multiple pads.

26. The instrument of claim 20, wherein the detector is an array of single detectors.

27. The instrument of claim 20, wherein the detector is a charge coupled device.

28. The instrument of claim 20, wherein the electromagnetic radiation emitted from the multiple pads comprises a Raman signal, an infrared (IR) signal, a fluorescence signal, or a luminescence signal.

29. The instrument of claim 20, wherein the interferometer comprises two arms to pass a portion of electromagnetic radiation emitted from the multiple pads through each of the two arms.

30. The instrument of claim 29, wherein one of the two arms comprises a phase shifter.

31. The instrument of claim 30, wherein the phase shifter comprises a variable index material.

32. The instrument of claim 20, wherein the interferometer comprises a MEMS based device, an optical bench, a wafer having optical structures, an optical splitter or an optical waveguide.

33. The instrument of claim 32, wherein the optical splitter or the optical waveguide comprises optical fibers coupled to each other to form the optical splitter or the optical guide.

34. The instrument of claim 32, wherein the optical bench comprises a MEMS based moving arm.

35. A method of collecting Fourier transform (FT) data, comprising:
illuminating a field of illumination in a plane containing a sample that emits an electromagnetic radiation, the field of illumination having a diameter greater than 1 microns, defocusing light from the illumination source with a secondary lens,
transforming the electromagnetic radiation emitted from the sample into an interferogram,
detecting an interferogram, and
transforming the interferogram into an emission spectrum by calculating Fourier transformation of the interfering patterns;
wherein FT data collection is performed without single spot scanning or without line scanning.

36. The method of claim 35, wherein the transforming the electromagnetic radiation emitted by the sample into an interferogram comprises creating the phase delay in the emission spectrum.

37. The method of claim 35, wherein the transforming the electromagnetic radiation emitted by the sample into an interferogram is performed by an interferometer.

38. The method of claim 35, wherein the detecting interferogram is performed by a detector and the transforming the interferogram into the emission spectrum is performed by a microprocessor.

39. The method of claim 38, wherein the detector is a charge coupled device.

40. The method of claim 36, wherein the interferometer comprises two arms to pass a portion of the electromagnetic radiation emitted from the sample through each of the two arms, further wherein one of the two arms comprises a phase shifter and the phase shifter comprises a variable index material.

41. The method of claim 36, wherein the interferometer comprises a MEMS based device, a wafer having optical structures, an optical splitter or an optical waveguide.

42. A method of collecting Fourier transform (FT) data, comprising:
illuminating a field of illumination in a plane containing a sample comprising an array of pads that emit an electromagnetic radiation, the field of illumination having an area greater than that of at least one pad of the array of pads, defocusing light from the illumination source with a secondary lens, transforming the electromagnetic radiation emitted from the sample into an interferogram, detecting the interferogram, and transforming the inteferogram into an emission spectrum; and wherein the FT data collection is performed without single spot scanning or without line scanning.

43. The method of claim 42, further comprising using a Bragg filter that substantially excludes JR signals and substantially passes Raman signals to the detector.

44. The method of claim 42, wherein the FT data comprises Raman data or fluorescence data.

45. A method of collecting Fourier Transform (FT) data with an optical imaging system, comprising:

simultaneously exposing to an illumination source multiple pads that emit light at one or more wavelengths different from the illumination wavelength;

defocusing light from the illumination source with a secondary lens;

directing the emitted light from the multiple pads along a predetermined optical path;

interferometrically sampling the emitted light and scanning a spectral range that includes the one or more wavelengths of the light emitted from the multiple pads;

detecting with a detector the emitted light from the multiple pads simultaneously; and collecting FT data corresponding to the detected light.

46. The method of claim 45, wherein the simultaneous exposing comprises expanding a beam emitted from a light source.

47. The method of claim 45, wherein the simultaneous exposing comprising generating light from multiple light sources.

48. The method of claim 45, wherein the simultaneous exposing comprises generating light from a single light source that is sufficiently spatially broad to expose said multiple pads simultaneously.

49. The method of claim 45, wherein the simultaneous exposing comprises generating a beam of light from a single light source and splitting the beam to provide multiple beams.

50. The method of claim 45, wherein the directing of the emitted light comprises collimating the emitted light.

51. The method of claim 45, wherein the directing of the emitted light along the optical path comprises reflecting the emitted light from the multiple pads along the optical path.

52. The method of claim 45, further comprising dichroically filtering the emitted light.

53. The method of claim 45, wherein interferometric sampling comprises directing a portion of the emitted light through an electro- or thermo-optical material for providing an optical path difference.

54. The method of claim 45, wherein the interferometric sampling comprises operating a Mach-Zehnder interferometer.

55. The method of claim 54, wherein the interferometric sampling comprises directing a portion of the emitted light through an electro- or thermo-optical material for providing an optical path difference.

56. The method of claim 45, wherein the FT data comprises Raman data or fluorescence data.

57. The method of claim 45, wherein the multiple pads comprise a biomolecule, a macromolecule, a nanomaterial, a capture molecule, Raman-active organic compound or a fluorescent compound.

58. The method of claim 45, further comprising removing light generated by the illumination source to prevent light generated by the illumination source from being received at the detector.

59. The method of claim 45, further comprising using a Bragg filter that substantially excludes JR signals emitted from the multiple pads and substantially passes Raman signals to the detector, wherein the multiple pads emit light at one or more wavelengths selected from the group consisting of IR, fluorescence, luminescence, and Raman.

60. The instrument of claim 13, wherein the interferometer comprises a Michelson interferometer wherein the Michelson interferometer comprises at least one movable mirror for adjusting an optical path difference.

61. The method of claim 45, wherein the interferometric sampling comprises operating a Michelson interferometer.

62. The method of claim 61, wherein the operating of the Michelson interferometer comprises adjusting at least one moveable mirror for adjusting an optical path difference.

* * * * *